(12) United States Patent
Gottlieb et al.

(10) Patent No.: US 9,265,455 B2
(45) Date of Patent: Feb. 23, 2016

(54) METHODS AND SYSTEMS FOR OPTIMIZING SENSOR FUNCTION BY THE APPLICATION OF VOLTAGE

(71) Applicant: Medtronic MiniMed, Inc., Northridge, CA (US)

(72) Inventors: Rebecca K. Gottlieb, Culver City, CA (US); Chia-Hung Chiu, Pasadena, CA (US); Ashwin K. Rao, Encino, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 539 days.

(21) Appl. No.: 13/675,813

(22) Filed: Nov. 13, 2012

(65) Prior Publication Data

US 2014/0135605 A1    May 15, 2014

(51) Int. Cl.
*A61B 5/145* (2006.01)
*A61B 5/00* (2006.01)
*A61B 5/055* (2006.01)
*A61B 5/1473* (2006.01)
*A61B 5/1495* (2006.01)
*A61B 5/1486* (2006.01)
*G01N 27/327* (2006.01)
*G01N 27/416* (2006.01)

(52) U.S. Cl.
CPC .......... *A61B 5/14532* (2013.01); *A61B 5/0004* (2013.01); *A61B 5/055* (2013.01); *A61B 5/1473* (2013.01); *A61B 5/1486* (2013.01); *A61B 5/1495* (2013.01); *A61B 5/742* (2013.01); *A61B 2560/0204* (2013.01); *A61B 2560/0223* (2013.01); *G01N 27/3274* (2013.01); *G01N 27/4163* (2013.01)

(58) Field of Classification Search
CPC .................................................... A61B 5/14532
USPC ....................................................... 73/114.74
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |

(Continued)

OTHER PUBLICATIONS

PCT International Search Report dated Mar. 7, 2014 for PCT application No. PCT/US2013/069887.

*Primary Examiner* — Hezron E Williams
*Assistant Examiner* — Mark A Shabman
(74) *Attorney, Agent, or Firm* — Gates & Cooper LLP

(57) ABSTRACT

A method is provided for initializing an analyte sensor, such as a glucose sensor. Where a sensor has been disconnected and reconnected, a disconnection time is determined and a sensor initialization protocol is selected based upon the disconnection time. The sensor initialization protocol may include applying a first series of voltage pulses to the sensor. A method for detecting hydration of a sensor is also provided.

22 Claims, 15 Drawing Sheets

(56) References Cited

U.S. PATENT DOCUMENTS

| | | |
|---|---|---|
| 6,379,301 B1 | 4/2002 | Worthington et al. |
| 6,424,847 B1 * | 7/2002 | Mastrototaro ..... A61B 5/14532 600/316 |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2005/0027177 A1 * | 2/2005 | Shin ................ A61B 5/14532 600/316 |
| 2007/0123819 A1 | 5/2007 | Mernoe et al. |
| 2007/0173712 A1 * | 7/2007 | Shah ................ A61B 5/14532 600/347 |
| 2008/0000779 A1 | 1/2008 | Wang et al. |
| 2010/0025238 A1 | 2/2010 | Gottlieb et al. |
| 2010/0160861 A1 | 6/2010 | Causey, III et al. |
| 2011/0230735 A1 | 9/2011 | Wolfe et al. |
| 2011/0230741 A1 * | 9/2011 | Liang et al. ................ 600/347 |

* cited by examiner

INITIALIZATION SCHEME 1

INITIALIZATION SCHEME 2

METHODS AND SYSTEMS FOR OPTIMIZING SENSOR FUNCTION BY THE APPLICATION OF VOLTAGE

BACKGROUND OF THE INVENTION

1. Field of the Invention

Analyte sensors (e.g. glucose sensors used in the management of diabetes) and methods and materials for making and using such sensors.

2. Description of Related Art

Analyte sensors such as biosensors include devices that use biological elements to convert a chemical analyte in a matrix into a detectable signal. There are many types of biosensors used for a wide variety of analytes. The most studied type of biosensor is the amperometric glucose sensor, which is crucial to the successful glucose level control for diabetes.

A typical glucose sensor works according to the following chemical reactions:

Equation 1

Equation 2

The glucose oxidase is used to catalyze the reaction between glucose and oxygen to yield gluconic acid and hydrogen peroxide (equation 1). The $H_2O_2$ reacts electrochemically as shown in equation 2, and the current can be measured by a potentiostat. These reactions, which occur in a variety of oxidoreductases known in the art, are used in a number of amperometric sensor designs.

As analyte sensor technology matures and new applications for sensor technology are developed, there is a need for methods and materials that facilitate the use of sensors in new technological applications. For example, hospitals increasingly use continuous glucose sensors to monitor patent physiology, for example in ICU environments. In such hospital environments, situations arise where a sensor must be disconnected from, and reconnected to, sensor electronics, for example, when a patient needs to undergo a magnetic resonance imaging (MRI) procedure. Because processors are incompatible with MRI, the sensor electronics need to be disconnected from the sensor until the MRI is completed.

In conventional sensor setups, if a sensor is disconnected from and then reconnected to sensor electronics, there is a significant delay before the sensor becomes stabilized enough to start sensing again. The delay can last from several minutes to a couple of hours, thereby complicating care in clinical settings. In addition, in individuals using analyte sensors in non-hospital settings (e.g. diabetics using glucose sensors to manage their disease), relatively long sensor initialization and/or start-up periods following sensor implantation can be problematical due to both the inconvenience to the user as well as the delayed receipt of information relating to user health. Because many diabetics do not have medical training, they may forgo optimal monitoring and modulation of blood glucose levels due to complexities associated with such management, for example, a two hour start-up period which can be an inconvenience in view of a patient's active daily routine.

For the above-noted reasons, methods and sensor systems that are designed to reduce sensor initialization and/or start-up times in are desirable.

SUMMARY OF THE INVENTION

The invention disclosed herein provides methods and systems for optimizing the initialization and performance of electrochemical analyte sensors that have been temporarily disconnected from the electronic components of their analyte monitoring systems. Embodiments of the invention are useful, for example, in situations where an implantable electrochemical glucose sensor is temporarily disconnected from the electronic components of an analyte monitoring systems during a hospital procedure such as a magnetic resonance imaging (MRI) procedure.

The invention disclosed herein has a number of embodiments. Embodiments of the invention include a method of initializing an electrochemical analyte sensor, the method comprising determining a disconnection time, wherein the disconnection time is the amount of time a sensor has been disconnected from sensor electronics, and then selecting an initialization protocol based on the disconnection time. In such embodiments, the initialization protocol selected from the group consisting of: a first initialization scheme comprising applying a first series of voltage pulses to the sensor and a second initialization scheme comprising applying a second series of voltage pulses to the sensor, wherein the first initialization scheme is selected if the disconnection time falls within a first time range and the second initialization scheme is selected if the disconnection time falls within a second time range. In such embodiments on can then apply the selected initialization protocol to the sensor. In some embodiments of the invention, the initialization protocol is selected from the group further consisting of a third initialization scheme comprising the application of no voltage to the sensor, wherein the third initialization scheme is selected if the disconnection time is less than the first time range and the second time range.

Different embodiments of the invention can utilize different disconnection time ranges that, for example, can depend upon the specific context in which a sensor is disconnected from sensor electronics. In some embodiments of the invention, the first time range can be, for example, greater than 120 minutes (e.g. a range of 120 minutes to at least 24 hours etc.). Similarly, in some embodiments of the invention, the second time range can be, for example, between 10 and 120 minutes.

In embodiments, the method further comprises applying a stabilization voltage to the sensor, after applying the selected initialization voltage, for a first stabilization time. The method may further include determining whether the sensor is stable after applying the first stabilization voltage; and if the sensor is not stable, applying a second stabilization voltage to the sensor for a second stabilization time. Example stabilization time periods include times less than forty minutes, such as 10, 16, 20, and 26 minutes, or 30 minutes. The second stabilization time may be the same or different than the first stabilization time.

Some embodiments of the invention include calibrating the sensor after the stabilization of the sensor, if the sensor is stable. Calibration may include measuring blood glucose using a blood glucose meter and correlating the value found to the sensor measurements. In some embodiments, the calibration of the sensor is only performed if the disconnection time falls within the first or second time range. In some embodiments of the invention, if the sensor is not stable after a predetermined maximum stabilization time, the initialization protocol is ended so that a new sensor may be connected to the sensor electronics. The predetermined maximum stabilization period may be 30 minutes. Other predetermined maximum stabilization periods are also possible, such as 35 or 40 minutes.

In embodiments, determining a disconnection time includes measuring the current output of the sensor and comparing the measured output to a disconnection threshold value. One possible threshold value is 0.6 nA. A sample range of potential threshold values is 1-10 nA. In embodiments, a timer inbuilt in the program records time of disconnection. The event of reconnection is detected when the current output is above a reconnection threshold, such as 4 nA.

In embodiments, the first initialization scheme includes the application of at least two voltages for a first predetermined initialization time. The at least two voltages may be pulsed, stepped or switched voltages. They may be applied in a repetitive sequence or each may be applied only once. Similarly, the second initialization scheme includes the application of at least two voltages for a second predetermined initialization time. The at least two voltages may be pulsed, stepped or switched voltages. They may be applied in a repetitive sequence or each may be applied only once. The predetermined second initialization time may be less than 30 minutes.

Some embodiments of the invention include detecting hydration of the sensor prior to applying the selected initiation protocol, wherein detecting hydration includes applying a series of hydration pulses to the sensor for a first hydration time; recording the current response of the sensor during application of the series of hydration pulses; and comparing the current response to a predetermined hydration threshold. Application of the series of hydration pulses may be terminated if the current response reaches or exceeds the predetermined hydration threshold. Detecting hydration may further include applying a second series of hydration pulses to the sensor for a second hydration time if the current response does not reach the predetermined hydration threshold during the first predetermined hydration time. The predetermined hydration threshold may be 100 nA or 50 nA, for example. Example hydration pulses may be a series of 0 V and 2 V pulses, for example for 20 seconds or 2 minutes each.

In some embodiments of the invention, the analyte sensing system further comprises a monitoring device in communication with the electronics device, wherein the monitoring device includes circuitry to monitor the signals received from the analyte sensor and to calculate the concentration of the analyte from the signals. The monitoring device may be connected directly to the sensor and/or sensor electronics or may receive data wirelessly. The sensor electronics may be part of the monitor or separate from the monitor.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE FIGURES

As shown in FIG. 20, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (isig) that is output from the potentiostat.

DETAILED DESCRIPTION OF THE EMBODIMENTS

Figure 1:
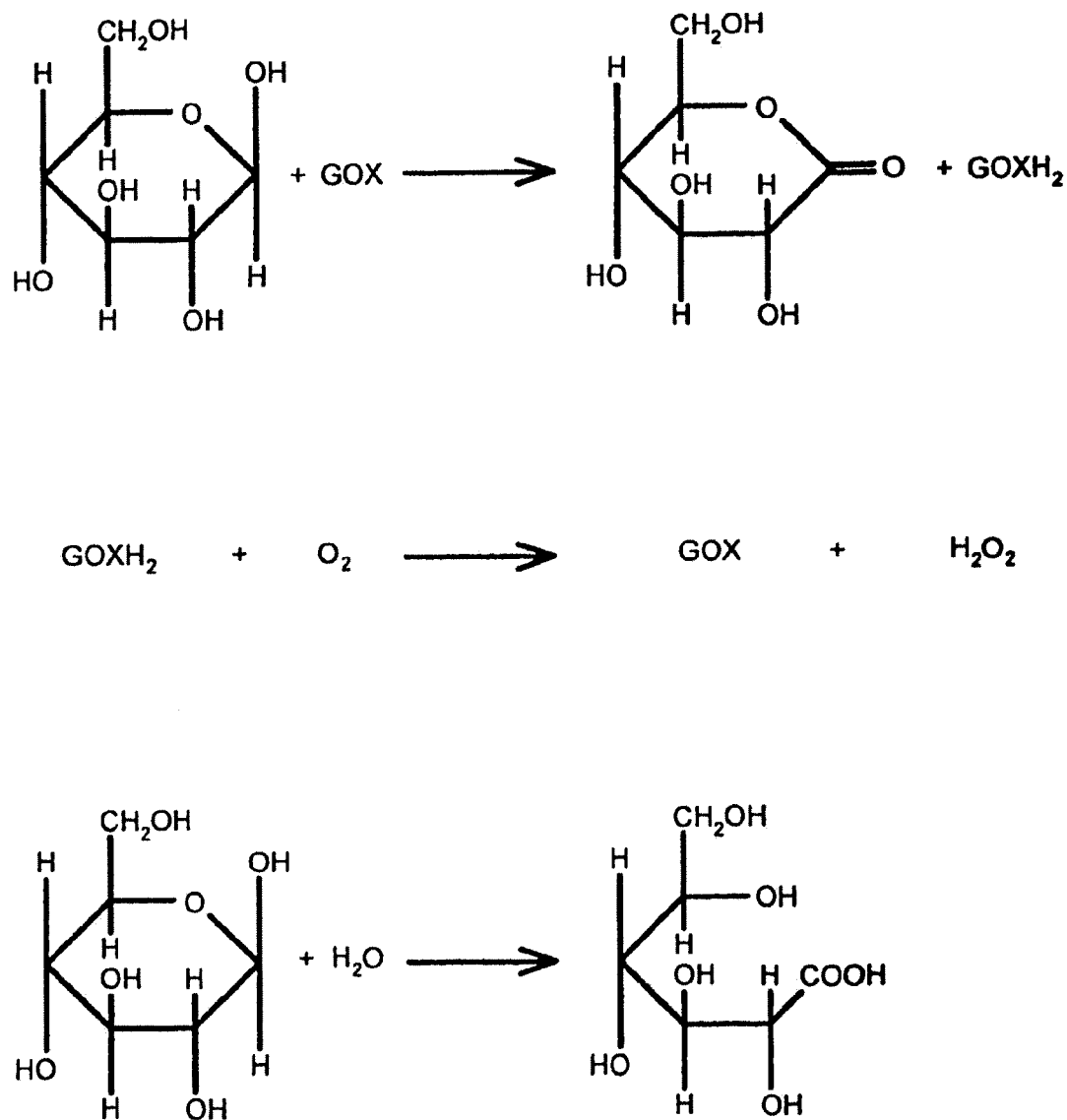
FIG. 1 provides a schematic of the well-known reaction between glucose and glucose oxidase. As shown in a stepwise manner, this reaction involves glucose oxidase (GOx), glucose and oxygen in water. In the reductive half of the reaction, two protons and electrons are transferred from 1-D-glucose to the enzyme yielding d-gluconolactone. In the oxidative half of the reaction, the enzyme is oxidized by molecular oxygen yielding hydrogen peroxide. The d-gluconolactone then reacts with water to hydrolyze the lactone ring and produce gluconic acid. In certain electrochemical sensors of the invention, the hydrogen peroxide produced by this reaction is oxidized at the working electrode ($H_2O_2 \rightarrow 2H^+ + O_2 + 2e^-$).

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

It is to be understood that this invention is not limited to the particular methodology, protocol and reagent described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "an oxidoreductase" includes a plurality of such oxidoreductases and equivalents thereof known to those skilled in the art, and so forth. All numbers recited in the specification and associated claims that refer to values that can be numerically characterized with a value other than a whole number (e.g. the concentration of a compound in a solution) are understood to be modified by the term "about".

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to, lactate. Salts, sugars, proteins fats, vitamins and hormones naturally occurring in blood or interstitial fluids can constitute analytes in certain embodiments. The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

The term "sensor," as used herein, is a broad term and is used in its ordinary sense, including, without limitation, the portion or portions of an analyte-monitoring device that detects an analyte. In one embodiment, the sensor includes an electrochemical cell that has a working electrode, a reference electrode, and optionally a counter electrode passing through and secured within the sensor body forming an electrochemically reactive surface at one location on the body, an electronic connection at another location on the body, and a membrane system affixed to the body and covering the electrochemically reactive surface. During general operation of the sensor, a biological sample (for example, blood or interstitial fluid), or a portion thereof, contacts (directly or after passage through one or more membranes or domains) an enzyme (for example, glucose oxidase); the reaction of the biological sample (or portion thereof results in the formation of reaction products that allow a determination of the analyte level in the biological sample.

The terms "electrical potential" and "potential" as used herein, are broad terms and are used in their ordinary sense, including, without limitation, the electrical potential difference between two points in a circuit which is the cause of the flow of a current. The term "system noise," as used herein, is a broad term and is used in its ordinary sense, including, without limitation, unwanted electronic or diffusion-related noise which can include Gaussian, motion-related, flicker, kinetic, or other white noise, for example.

As discussed in detail below, embodiments of the invention relate to the use of an electrochemical sensor that measures a concentration of an analyte of interest or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors typically comprise a membrane surrounding the enzyme through which an analyte migrates. The product is then measured using electrochemical methods and thus the output of an electrode system functions as a measure of the analyte.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their biospecificity. Embodiments of the invention described herein can be adapted and implemented with a wide variety of known electrochemical sensors, including for example, U.S. Patent Application No. 20050115832, U.S. Pat. Nos. 6,001, 067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391, 250, 5,482,473, 5,299,571, 5,568,806, 5,494,562, 6,120,676, 6,542,765, 7,033,336 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042,625, and WO 03/074107, and European Patent Application EP 1153571, the contents of each of which are incorporated herein by reference.

While some embodiments of the invention pertain to glucose and/or lactate sensors, the methods disclosed herein can be adapted for use with any one of the wide variety of sensors known in the art. The analyte sensor elements, architectures and methods for making and using these elements that are disclosed herein can be used to establish a variety of layered sensor structures. Such sensors of the invention exhibit a surprising degree of flexibility and versatility, characteristics which allow a wide variety of sensor configurations to be designed to examine a wide variety of analyte species.

In typical embodiments of the present invention, the transduction of the analyte concentration into a processable signal is by electrochemical means. These transducers may include any of a wide variety of amperometric, potentiometric, or conductimetric base sensors known in the art. Moreover, the microfabrication sensor techniques and materials of the instant invention may be applied to other types of transducers (e.g., acoustic wave sensing devices, thermistors, gas-sensing electrodes, field-effect transistors, optical and evanescent field wave guides, and the like) fabricated in a substantially nonplanar, or alternatively, a substantially planar manner. A useful discussion and tabulation of transducers which may be exploited in a biosensor as well as the kinds of analytical applications in which each type of transducer or biosensor, in general, may be utilized, is found in an article by Christopher R. Lowe in Trends in Biotech. 1984, 2(3), 59-65.

Specific aspects of embodiments of the invention are discussed in detail in the following sections.

I. Typical Elements, Configurations and Analyte Sensor Embodiments of the Invention

A. Typical Architectures Found in of Embodiments of the Invention

Figure 2:
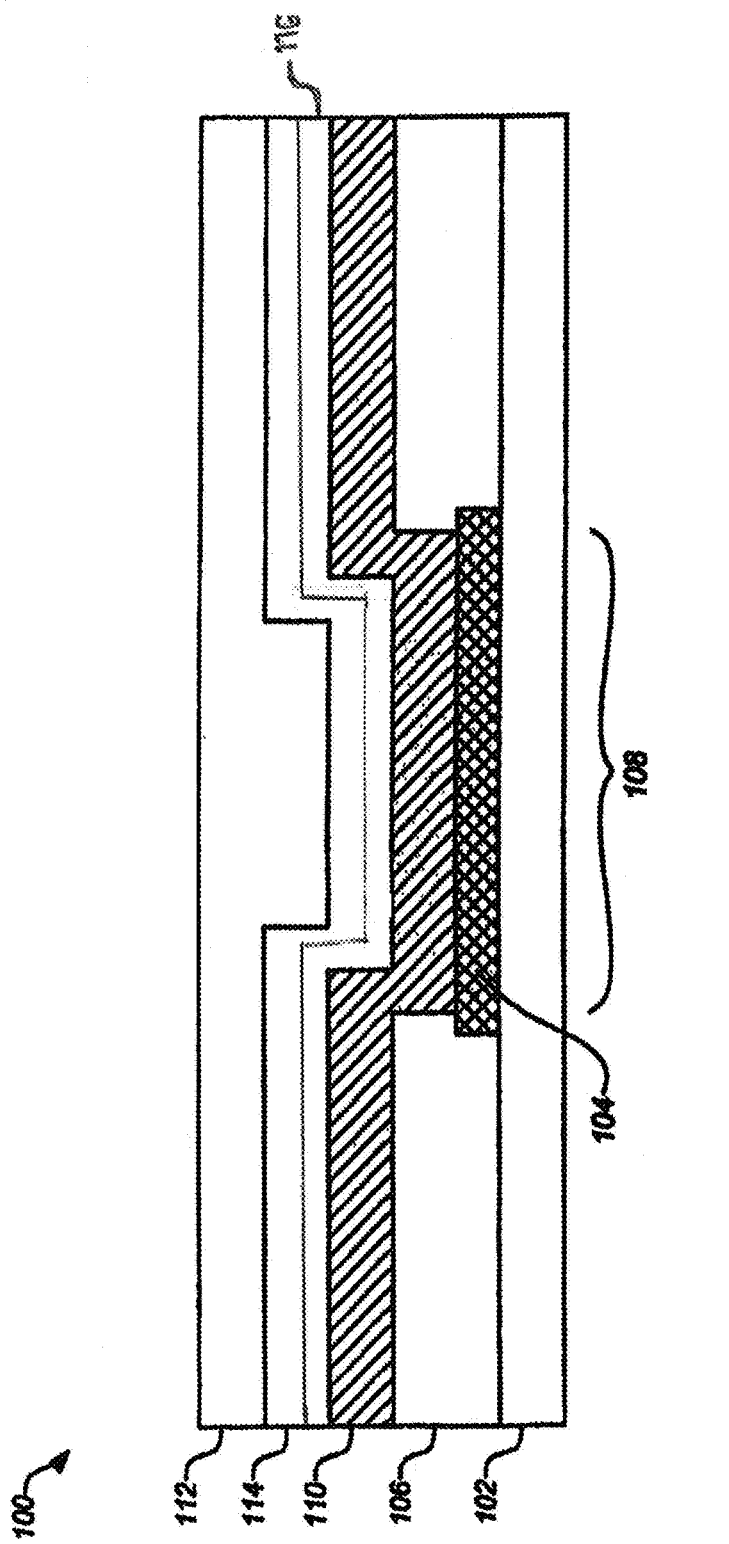
FIG. 2 provides a diagrammatic view of a typical layered analyte sensor configuration of the current invention.

FIG. 2 illustrates a cross-section of a typical sensor embodiment 100 of the present invention. This sensor embodiment is formed from a plurality of components that are typically in the form of layers of various conductive and non-conductive constituents disposed on each other according to art accepted methods and/or the specific methods of the invention disclosed herein. The components of the sensor are typically characterized herein as layers because, for example, it allows for a facile characterization of the sensor structure shown in FIG. 2. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 2 includes a base layer 102 to support the sensor 100. The base layer 102 can be made of a material such as a metal and/or a ceramic and/or a polymeric substrate, which may be self-supporting or further supported by another material as is known in the art. Embodiments of the invention include a conductive layer 104 which is disposed on and/or combined with the base layer 102. Typically the conductive layer 104 comprises one or more electrodes. An operating sensor 100 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 102 and/or conductive layer 104 can be generated using many known techniques and materials. In certain embodiments of the invention, the electrical circuit of the sensor is defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating cover layer 106 such as a polymer coating can be disposed on portions of the sensor 100. Acceptable polymer coatings for use as the insulating protective cover layer 106 can include, but are not limited to, non-toxic biocompatible polymers such as silicone compounds, polyimides, biocompatible solder masks, epoxy acrylate copolymers, or the like. In the sensors of the present invention, one or more exposed regions or apertures 108 can be made through the cover layer 106 to open the conductive layer 104 to the external environment and to, for example, allow an analyte such as glucose to permeate the layers of the sensor and be sensed by the sensing elements. Apertures 108 can be formed by a number of techniques, including laser ablation, tape masking, chemical milling or etching or photolithographic development or the like. In certain embodiments of the invention, during manufacture, a secondary photoresist can also be applied to the protective layer 106 to define the regions of the protective layer to be removed to form the aperture(s) 108. The exposed electrodes and/or contact pads can also undergo secondary processing (e.g. through the apertures 108), such as additional plating processing, to prepare the surfaces and/or strengthen the conductive regions.

In the sensor configuration shown in FIG. 2, an analyte sensing layer 110 (which is typically a sensor chemistry layer, meaning that materials in this layer undergo a chemical reaction to produce a signal that can be sensed by the conductive layer) is disposed on one or more of the exposed electrodes of the conductive layer 104. Typically, the analyte sensing layer 110 is an enzyme layer. Most typically, the analyte sensing layer 110 comprises an enzyme capable of producing and/or utilizing oxygen and/or hydrogen peroxide, for example the enzyme glucose oxidase. Optionally the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic Diabetes.

In embodiments of the invention, the analyte sensing layer 110 can be applied over portions of the conductive layer or over the entire region of the conductive layer. Typically the analyte sensing layer 110 is disposed on the working electrode which can be the anode or the cathode. Optionally, the analyte sensing layer 110 is also disposed on a counter and/or reference electrode. While the analyte sensing layer 110 can be up to about 1000 microns (μm) in thickness, typically the analyte sensing layer is relatively thin as compared to those found in sensors previously described in the art, and is for example, typically less than 1, 0.5, 0.25 or 0.1 microns in thickness. As discussed in detail below, some methods for generating a thin analyte sensing layer 110 include brushing the layer onto a substrate (e.g. the reactive surface of a platinum black electrode), as well as spin coating processes, dip and dry processes, low shear spraying processes, ink jet printing processes, silk screen processes and the like. In certain embodiments of the invention, brushing is used to: (1) allow for a precise localization of the layer; and (2) push the layer deep into the architecture of the reactive surface of an electrode (e.g. platinum black produced by an electrodeposition process).

Typically, the analyte sensing layer 110 is coated and or disposed next to one or more additional layers. Optionally, the one or more additional layers includes a protein layer 116 disposed upon the analyte sensing layer 110. Typically, the protein layer 116 comprises a protein such as human serum albumin, bovine serum albumin or the like. Typically, the protein layer 116 comprises human serum albumin. In some embodiments of the invention, an additional layer includes an analyte modulating layer 112 that is disposed above the analyte sensing layer 110 to regulate analyte contact with the analyte sensing layer 110. For example, the analyte modulating membrane layer 112 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art.

In some embodiments of the invention, the architecture or thickness of a sensor layer is used to optimize a property of the sensor. For example in some embodiments of the invention, the elongated base layer is comprised of a dielectric or polyimide ceramic material that is at least 100 microns thick. In some embodiments of the invention, the analyte modulating layer is at least 6, 7, 8, 9, 10, 15, 20, 25 or 30 microns thick. Certain embodiments of the invention use a thick layer (e.g. 25 or 30 microns) of an analyte modulating layer because in such embodiments, this thick layer is observed to both optimize the linearity of an analyte signal over a range of signals (e.g. glucose concentration). Such thick layers have further properties that are desirable in certain embodiments of the invention, for example a longer analyte modulating layer lifetime (e.g. due to the extra material), a property that makes them particularly suited for certain long term sensor embodiments.

In typical embodiments of the invention, an adhesion promoter layer 114 is disposed between the analyte modulating layer 112 and the analyte sensing layer 110 as shown in FIG. 2 in order to facilitate their contact and/or adhesion. In a specific embodiment of the invention, an adhesion promoter layer 114 is disposed between the analyte modulating layer 112 and the protein layer 116 as shown in FIG. 2 in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the analyte sensing layer 110 can be sufficiently crosslinked or otherwise prepared to allow the analyte modulating membrane layer 112 to be disposed in direct contact with the analyte sensing layer 110 in the absence of an adhesion promoter layer 114.

In certain embodiments of the invention, a sensor is designed to include additional layers such as an interference rejection layer discussed below.

B. Typical Analyte Sensor Constituents Used in Embodiments of the Invention

The following disclosure provides examples of typical elements/constituents used in sensor embodiments of the invention. While these elements can be described as discreet units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described below.

Base Constituent

Sensors of the invention typically include a base constituent (see, e.g. element 102 in FIG. 2). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like.

The base constituent may be self-supporting or further supported by another material as is known in the art. In one embodiment of the sensor configuration shown in FIG. 2, the base constituent 102 comprises a ceramic. Alternatively, the base constituent comprises a polymeric material such as a polyimide. In an illustrative embodiment, the ceramic base comprises a composition that is predominantly $Al_2O_3$ (e.g. 96%). The use of alumina as an insulating base constituent for use with implantable devices is disclosed in U.S. Pat. Nos. 4,940,858, 4,678,868 and 6,472,122 which are incorporated herein by reference. The base constituents of the invention can further include other elements known in the art, for example hermetical vias (see, e.g. WO 03/023388). Depending upon the specific sensor design, the base constituent can be relatively thick constituent (e.g. thicker than 50, 100, 200, 300, 400, 500 or 1000 microns). Alternatively, one can utilize a nonconductive ceramic, such as alumina, in thin constituents, e.g., less than about 30 microns.

Conductive Constituent

The electrochemical sensors of the invention typically include a conductive constituent disposed upon the base constituent that includes at least one electrode for contacting an analyte or its byproduct (e.g. oxygen and/or hydrogen peroxide) to be assayed (see, e.g. element 104 in FIG. 2). The term "conductive constituent" is used herein according to art accepted terminology and refers to electrically conductive sensor elements such as electrodes which are capable of measuring and a detectable signal and conducting this to a detection apparatus. An illustrative example of this is a conductive constituent that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 110 or a reaction product of this interaction (e.g. hydrogen peroxide). Illustrative examples of such elements include electrodes which are capable of producing variable detectable signals in the presence of variable concentrations of molecules such as hydrogen peroxide or oxygen. Typically one of these electrodes in the conductive constituent is a working electrode, which can be made from non-corroding metal or carbon. A carbon working electrode may be vitreous or graphitic and can be made from a solid or a paste. A metallic working electrode may be made from platinum group metals, including palladium or gold, or a non-corroding metallically conducting oxide, such as ruthenium dioxide. Alternatively the electrode may comprise a silver/silver chloride electrode composition. The working electrode may be a wire or a thin conducting film applied to a substrate, for example, by coating or printing. Typically, only a portion of the surface of the metallic or carbon conductor is in electrolytic contact with the analyte-containing solution. This portion is called the working surface of the electrode. The remaining surface of the electrode is typically isolated from the solution by an electrically insulating cover constituent 106. Examples of useful materials for generating this protective cover constituent 106 include polymers such as polyimides, polytetrafluoroethylene, polyhexafluoropropylene and silicones such as polysiloxanes.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate. Optionally, the electrodes can be disposed on a single surface or side of the sensor structure. Alternatively, the electrodes can be disposed on a multiple surfaces or sides of the sensor structure (and can for example be connected by vias through the sensor material(s) to the surfaces on which the electrodes are disposed). In certain embodiments of the invention, the reactive surfaces of the electrodes are of different relative areas/sizes, for example a 1× reference electrode, a 2.6× working electrode and a 3.6× counter electrode.

Typically for in vivo use, embodiments of the present invention are implanted subcutaneously in the skin of a mammal, such as a person, for direct contact with the body fluids of the mammal, such as blood. Alternatively the sensors can be implanted into other regions within the body of a mammal such as in the intraperotineal space. When multiple working electrodes are used, they may be implanted together or at different positions in the body. The counter, reference, and/or counter/reference electrodes may also be implanted either proximate to the working electrode(s) or at other positions within the body of the mammal. Embodiments of the invention include sensors comprising electrodes constructed from nanostructured materials. As used herein, a "nanostructured material" is an object manufactured to have at least one dimension smaller than 100 nm. Examples include, but are not limited to, single-walled nanotubes, double-walled nanotubes, multi-walled nanotubes, bundles of nanotubes, fullerenes, cocoons, nanowires, nanofibres, onions and the like.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size). Examples of interference rejection constituents include one or more layers or coatings of compounds such as hydrophilic polyurethanes, cellulose acetate (including cellulose acetate incorporating agents such as poly (ethylene glycol), polyethersulfones, polytetra-fluoroethylenes, the perfluoronated ionomer Nafion™, polyphenylenediamine, epoxy and the like. In particular embodiments, the interference rejection constituents are comprised of a NAFION (a sulfonated tetrafluorethylene copolymer having the molecular formula C7HF13O5S. C2F4, CAS number [31175-20-9]) and/or a cellulose acetate composition. Illustrative discussions of such interference rejection constituents are found for example in Ward et al., Biosensors and Bioelectronics 17 (2002) 181-189 and Choi et al., Analytical Chimica Acta 461 (2002) 251-260 which are incorporated herein by reference. Other interference rejection constituents include for example those observed to limit the movement of compounds based upon a molecular weight range, for example cellulose acetate as disclosed for example in U.S. Pat. No. 5,755,939, the contents of which are incorporated by reference.

An interference rejection membrane (IRM) may comprise NAFION and its effectiveness at inhibiting interfering signals that can be generated by acetominophenol in an amperometric sensor. Typically, an IRM is disposed under an analyte sensing layer (e.g. one comprising glucose oxidase). In certain embodiments of the invention, the IRM is disposed between the reactive surface of an electrode and an analyte sensing layer. Related embodiments of the invention include methods for inhibiting one or more signals generated by an interfering compound in various sensor embodiments of the invention (e.g. by using an interference rejection layer).

Analyte Sensing Constituent

The electrochemical sensors of the invention include an analyte sensing constituent disposed on the electrodes of the sensor (see, e.g. element 110 in FIG. 2). The term "analyte sensing constituent" is used herein according to art accepted terminology and refers to a constituent comprising a material that is capable of recognizing or reacting with an analyte whose presence is to be detected by the analyte sensor apparatus. Typically this material in the analyte sensing constituent produces a detectable signal after interacting with the analyte to be sensed, typically via the electrodes of the conductive constituent. In this regard the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide according to the reaction shown in FIG. 1, wherein the hydrogen peroxide so generated is anodically detected at the working electrode in the conductive constituent.

As noted above, the enzyme and the second protein (e.g. an albumin) are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture. The addition of a cross-linking reagent to the protein mixture creates a protein paste. The concentration of the cross-linking reagent to be added may vary according to the concentration of the protein mixture. While glutaraldehyde is an illustrative crosslinking reagent, other cross-linking reagents may also be used or may be used in place of glutaraldehyde. Other suitable cross-linkers also may be used, as will be evident to those skilled in the art.

The GOx and/or carrier protein concentration may vary for different embodiments of the invention. For example, the GOx concentration may be within the range of approximately 50 mg/ml (approximately 10,000 U/ml) to approximately 700 mg/ml (approximately 150,000 U/ml). Typically the GOx concentration is about 115 mg/ml (approximately 22,000 U/ml). In such embodiments, the HSA concentration may vary between about 0.5%-30% (w/v), depending on the GOx concentration. Typically the HSA concentration is about 1-10% w/v, and most typically is about 5% w/v. In alternative embodiments of the invention, collagen or BSA or other structural proteins used in these contexts can be used instead of or in addition to HSA. Although GOx is discussed as an illustrative enzyme in the analyte sensing constituent, other proteins and/or enzymes may also be used or may be used in place of GOx, including, but not limited to glucose dehydrogenase or hexokinase, hexose oxidase, lactate oxidase, and the like. Other proteins and/or enzymes may also be used, as will be evident to those skilled in the art. Moreover, although HSA is employed in the example embodiment, other structural proteins, such as BSA, collagens or the like, could be used instead of or in addition to HSA.

As noted above, in some embodiments of the invention, the analyte sensing constituent includes a composition (e.g. glucose oxidase) capable of producing a signal (e.g. a change in oxygen and/or hydrogen peroxide concentrations) that can be sensed by the electrically conductive elements (e.g. electrodes which sense changes in oxygen and/or hydrogen peroxide concentrations). However, other useful analyte sensing constituents can be formed from any composition that is capable of producing a detectable signal that can be sensed by the electrically conductive elements after interacting with a target analyte whose presence is to be detected. In some embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; Jan. 7, 1991) the entire contents of which are incorporated herein by reference.

Other useful analyte sensing constituents can be formed to include antibodies whose interaction with a target analyte is capable of producing a detectable signal that can be sensed by the electrically conductive elements after interacting with the target analyte whose presence is to be detected. Examples of anti-body-based apparatuses are found in U.S. Pat. Nos. 5,427,912, 5,149,630, 6,410,251, and 4,402,819, which are incorporated herein by reference. For related disclosures, see also U.S. Pat. Nos. 6,703,210, 5,981,203, 5,705,399 and 4,894,253, which are incorporated herein by reference.

In addition to enzymes and antibodies, other exemplary materials for use in the analyte sensing constituents of the sensors disclosed herein include polymers that bind specific types of cells or cell components (e.g. polypeptides, carbohydrates and the like); single-strand DNA; antigens and the like. The detectable signal can be, for example, an optically detectable change, such as a color change or a visible accumulation of the desired analyte (e.g., cells). Sensing elements can also be formed from materials that are essentially non-reactive (i.e., controls). The foregoing alternative sensor elements are beneficially included, for example, in sensors for use in cell-sorting assays and assays for the presence of pathogenic organisms, such as viruses (HIV, hepatitis-C, etc.), bacteria, protozoa and the like.

Also contemplated are analyte sensors that measure an analyte that is present in the external environment and that can in itself produce a measurable change in current at an electrode. In sensors measuring such analytes, the analyte sensing constituent can be optional.

Protein Constituent

The electrochemical sensors of the invention optionally include a protein constituent disposed between the analyte sensing constituent and the analyte modulating constituent (see, e.g. element 116 in FIG. 2). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 114 in FIG. 2). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

The use of silane coupling reagents, especially those of the formula $R'Si(OR)_3$ in which R' is typically an aliphatic group with a terminal amine and R is a lower alkyl group, to promote adhesion is known in the art (see, e.g. U.S. Pat. No. 5,212,050, which is incorporated herein by reference). For example, chemically modified electrodes in which a silane such as γ-aminopropyltriethoxysilane and glutaraldehyde were used in a step-wise process to attach and to co-crosslink bovine serum albumin (BSA) and glucose oxidase (GOx) to the electrode surface are well known in the art (see, e.g. Yao, T. Analytica Chim. Acta 1983, 148, 27-33).

In certain embodiments of the invention, the adhesion promoting constituent further comprises one or more compounds that can also be present in an adjacent constituent such as the polydimethyl siloxane (PDMS) compounds that serves to limit the diffusion of analytes such as glucose through the analyte modulating constituent. In illustrative embodiments the formulation comprises 0.5-20% PDMS, typically 5-15% PDMS, and most typically 10% PDMS. In certain embodiments of the invention, the adhesion promoting constituent is crosslinked within the layered sensor system and correspondingly includes an agent selected for its ability to crosslink a moiety present in a proximal constituent such as the analyte modulating constituent. In illustrative embodiments of the invention, the adhesion promoting constituent includes an agent selected for its ability to crosslink an amine or carboxyl moiety of a protein present in a proximal constituent such a the analyte sensing constituent and/or the protein constituent and or a siloxane moiety present in a compound disposed in a proximal layer such as the analyte modulating layer. Optionally, a first compound in the adhesion promoting layer is crosslinked to a second compound in the analyte sensing layer.

Analyte Modulating Constituent

The electrochemical sensors of the invention include an analyte modulating constituent disposed on the sensor (see, e.g. element 112 in FIG. 2). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferants, such as ascorbic acid and uric acid, diffuse through a primary membrane of the sensor. As the glucose, oxygen and interferants reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The sensor membrane assembly serves several functions, including selectively allowing the passage of glucose therethrough. In this context, an illustrative analyte modulating constituent is a semi-permeable membrane which permits passage of water, oxygen and at least one selective analyte and which has the ability to absorb water, the membrane having a water soluble, hydrophilic polymer.

A variety of illustrative analyte modulating compositions are known in the art and are described for example in U.S. Pat. Nos. 6,319,540, 5,882,494, 5,786,439 5,777,060, 5,771,868 and 5,391,250, the disclosures of each being incorporated herein by reference. The hydrogels described therein are particularly useful with a variety of implantable devices for which it is advantageous to provide a surrounding water constituent. In some embodiments of the invention, the analyte modulating composition includes PDMS. In certain embodiments of the invention, the analyte modulating constituent includes an agent selected for its ability to crosslink a siloxane moiety present in a proximal constituent. In closely related embodiments of the invention, the adhesion promoting constituent includes an agent selected for its ability to crosslink an amine or carboxyl moiety of a protein present in a proximal constituent.

In some embodiments of the invention, a hydrophilic analyte modulating layer is coated over at least 50, 75% or 100% of the reactive surface of an electrode (e.g. an electrically conductive wire).

Cover Constituent

The electrochemical sensors of the invention include one or more cover constituents which are typically electrically insulating protective constituents (see, e.g. element 106 in FIG. 2). Typically, such cover constituents can be in the form of a coating, sheath or tube and are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

C. Typical Analyte Sensor System Embodiments of the Invention

Embodiments of the sensor elements and sensors can be operatively coupled to a variety of other systems elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

Embodiments of the invention include devices which display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g. a glucose sensor).

An illustrative system embodiment consists of a glucose sensor, a transmitter and pump receiver and a glucose meter. In this system, radio signals from the transmitter can be sent to the pump receiver every 5 minutes to provide providing real-time sensor glucose (SG) values. Values/graphs are displayed on a monitor of the pump receiver so that a user can self monitor blood glucose and deliver insulin using their own insulin pump. Typically an embodiment of device disclosed herein communicates with a second medical device via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically in such devices, the physiological characteristic values include a plurality of measurements of blood glucose.

Figure 3:
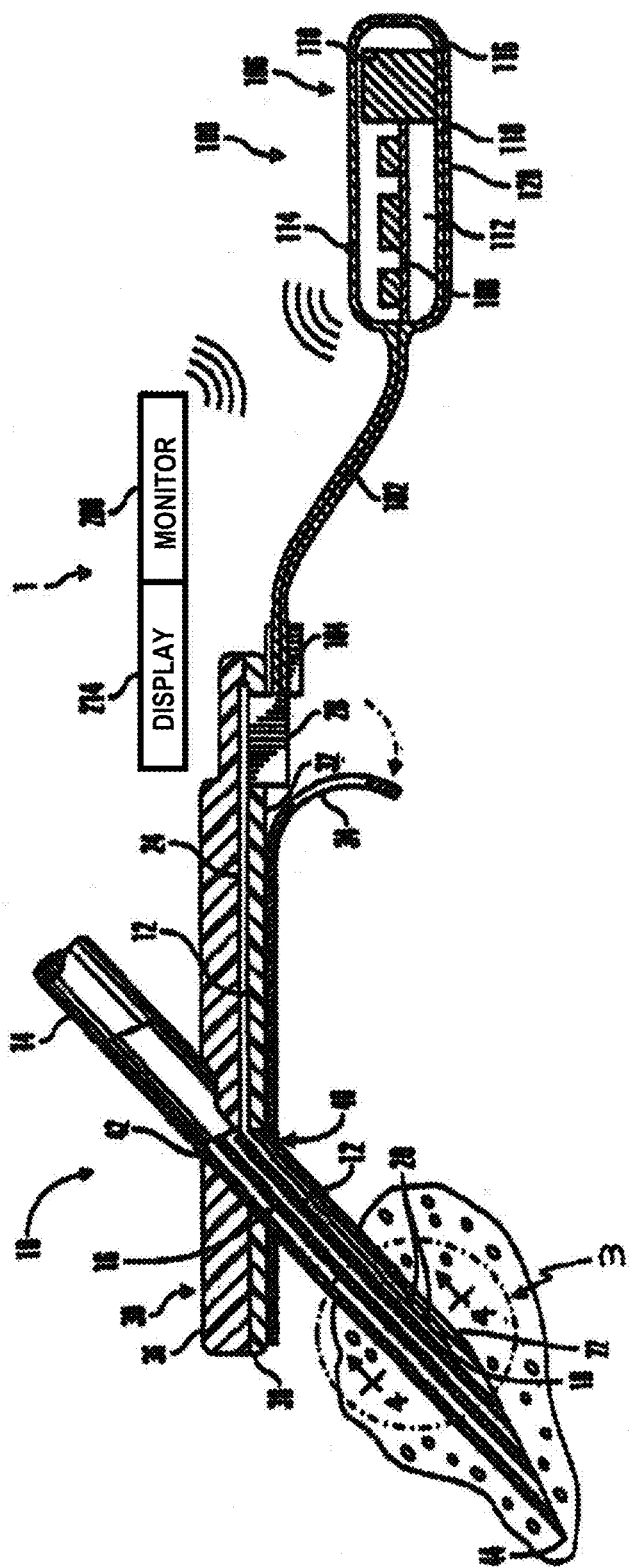
FIG. 3 provides a perspective view illustrating a subcutaneous sensor insertion set, a telemetered characteristic monitor transmitter device, and a data receiving device embodying features of the invention.

FIG. 3 provides a perspective view of one generalized embodiment of subcutaneous sensor insertion system and a block diagram of a sensor electronics device according to one illustrative embodiment of the invention. Additional elements typically used with such sensor system embodiments are disclosed for example in U.S. Patent Application No. 20070163894, the contents of which are incorporated by reference. FIG. 3 provides a perspective view of a telemetered characteristic monitor system 1, including a subcutaneous sensor set 10 provided for subcutaneous placement of an active portion of a flexible sensor 12, or the like, at a selected site in the body of a user. The subcutaneous or percutaneous portion of the sensor set 10 includes a hollow, slotted insertion needle 14 having a sharpened tip 44, and a cannula 16. Inside the cannula 16 is a sensing portion 18 of the sensor 12 to expose one or more sensor electrodes 20 to the user's bodily fluids through a window 22 formed in the cannula 16. The sensing portion 18 is joined to a connection portion 24 that terminates in conductive contact pads, or the like, which are also exposed through one of the insulative layers. The connection portion 24 and the contact pads are generally adapted for a direct wired electrical connection to a suitable monitor 200 coupled to a display 214 for monitoring a user's condition in response to signals derived from the sensor electrodes 20. The connection portion 24 may be conveniently connected electrically to the monitor 200 or a characteristic monitor transmitter 100 by a connector block 28 (or the like) as shown and described in U.S. Pat. No. 5,482,473, entitled FLEX CIRCUIT CONNECTOR, which is incorporated by reference. In typical embodiments of the invention, a contact pad and an electrode are at least, 15, 16, 17, 18, 19, 20, 21, 22, 23, 24 or 25 millimeters apart.

As shown in FIG. 3, in accordance with embodiments of the present invention, subcutaneous sensor set 10 may be configured or formed to work with either a wired or a wireless characteristic monitor system. The proximal part of the sensor 12 is mounted in a mounting base 30 adapted for placement onto the skin of a user. The mounting base 30 can be a pad having an underside surface coated with a suitable pressure sensitive adhesive layer 32, with a peel-off paper strip 34 normally provided to cover and protect the adhesive layer 32, until the sensor set 10 is ready for use. The mounting base 30 includes upper and lower layers 36 and 38, with the connection portion 24 of the flexible sensor 12 being sandwiched between the layers 36 and 38. The connection portion 24 has a forward section joined to the active sensing portion 18 of the sensor 12, which is folded angularly to extend downwardly through a bore 40 formed in the lower base layer 38. Optionally, the adhesive layer 32 (or another portion of the apparatus in contact with in vivo tissue) includes an anti-inflammatory agent to reduce an inflammatory response and/or anti-bacterial agent to reduce the chance of infection. The insertion needle 14 is adapted for slide-fit reception through a needle port 42 formed in the upper base layer 36 and through the lower bore 40 in the lower base layer 38. After insertion, the insertion needle 14 is withdrawn to leave the cannula 16 with the sensing portion 18 and the sensor electrodes 20 in place at the selected insertion site. In this embodiment, the telemetered characteristic monitor transmitter 100 is coupled to a sensor set 10 by a cable 102 through a connector 104 that is electrically coupled to the connector block 28 of the connector portion 24 of the sensor set 10.

In the embodiment shown in FIG. 3, the telemetered characteristic monitor 100 includes a housing 106 that supports a printed circuit board 108, batteries 110, antenna 112, and the cable 102 with the connector 104. In some embodiments, the housing 106 is formed from an upper case 114 and a lower case 116 that are sealed with an ultrasonic weld to form a waterproof (or resistant) seal to permit cleaning by immersion (or swabbing) with water, cleaners, alcohol or the like. In some embodiments, the upper and lower case 114 and 116 are formed from a medical grade plastic. However, in alternative embodiments, the upper case 114 and lower case 116 may be connected together by other methods, such as snap fits, sealing rings, RTV (silicone sealant) and bonded together, or the like, or formed from other materials, such as metal, composites, ceramics, or the like. In other embodiments, the separate case can be eliminated and the assembly is simply potted in epoxy or other moldable materials that is compatible with the electronics and reasonably moisture resistant. As shown, the lower case 116 may have an underside surface coated with a suitable pressure sensitive adhesive layer 118, with a peel-off paper strip 120 normally provided to cover and protect the adhesive layer 118, until the sensor set telemetered characteristic monitor transmitter 100 is ready for use.

In the illustrative embodiment shown in FIG. 3, the subcutaneous sensor set 10 facilitates accurate placement of a flexible thin film electrochemical sensor 12 of the type used for monitoring specific blood parameters representative of a user's condition. The sensor 12 monitors glucose levels in the body, and may be used in conjunction with automated or semi-automated medication infusion pumps of the external or implantable type as described in U.S. Pat. No. 4,562,751; 4,678,408; 4,685,903 or 4,573,994, to control delivery of insulin to a diabetic patient.

In the illustrative embodiment shown in FIG. 3, the sensor electrodes 10 may be used in a variety of sensing applications and may be configured in a variety of ways. For example, the sensor electrodes 10 may be used in physiological parameter sensing applications in which some type of biomolecule is used as a catalytic agent. For example, the sensor electrodes 10 may be used in a glucose and oxygen sensor having a glucose oxidase enzyme catalyzing a reaction with the sensor electrodes 20. The sensor electrodes 10, along with a biomolecule or some other catalytic agent, may be placed in a human body in a vascular or non-vascular environment. For example, the sensor electrodes 20 and biomolecule may be placed in a vein and be subjected to a blood stream, or may be placed in a subcutaneous or peritoneal region of the human body.

In the embodiment of the invention shown in FIG. 3, the monitor of sensor signals 200 may also be referred to as a sensor electronics device 200. The monitor 200 may include a power source, a sensor interface, processing electronics (i.e. a processor), and data formatting electronics. The monitor 200 may be coupled to the sensor set 10 by a cable 102 through a connector that is electrically coupled to the connector block 28 of the connection portion 24. In an alternative embodiment, the cable may be omitted. In this embodiment of the invention, the monitor 200 may include an appropriate connector for direct connection to the connection portion 104 of the sensor set 10. The sensor set 10 may be modified to have the connector portion 104 positioned at a different location, e.g., on top of the sensor set to facilitate placement of the monitor 200 over the sensor set.

D. Embodiments of the Invention and Associated Characteristics

Embodiments of the invention disclosed herein focus on implantable analyte sensors and sensor systems that are designed to include elements and/or configurations of elements that facilitate sensor initialization and/or start-up times in vivo, for example, the time that it takes for a sensor to settle into its environment (e.g. become appropriately hydrated), and/or begin to sense analyte concentrations and/or start transmitting meaningful information to a user. As discussed further herein, it is known in the art that the amount time required for sensor initialization and/or start-up prior to its use can be relatively long (e.g. in amperometric glucose sensors, the sensor start-up initialization times can range from 2 to 10 hours), a factor which can hinder the use of such sensors in the administration of medical care. For example, in hospital settings, a relatively long sensor initialization and/or start-up period can delay the receipt of important information relating to patient health (e.g. hyperglycemia or hypoglycemia in a diabetic patient), thereby delaying treatments predicated on the receipt of such information (e.g. the administration of insulin).

In addition, a relatively long sensor initialization and/or start-up period in hospital settings can require repeated monitoring by hospital staff, a factor which contributes to the costs of patient care. Moreover, these long initialization times can also be a problem if a sensor needs to be removed from sensor electronics and then connected again, for example for an MRI procedure where the sensor electronics are not compatible. In this context, electronic processing and/or telemetering is typically employed with the amperometric sensors, which are, for example, useful for buffering the electrical signals produced by the sensors, processing the sensor signals for transmission, and communicating the buffered, processing signals via a link to a monitoring unit etc.

Sensors having reduced initialization and/or start-up times in vivo in hospital settings and sensors and sensor systems that are designed to include elements and/or configurations of elements that diminish long sensor initialization and/or start-up times are highly desirable. With glucose sensors for example, even a 15-30 minute reduction of sensor initialization and/or start-up time is highly desirable because, for example, such shorter initialization times can: (1) reduce the need for patient monitoring by hospital personnel, a factor which contributes to the cost-effectiveness of such medical devices; and (2) reduce delays in the receipt of important information relating to patient health. It is further desirable to reduce the initialization time even further for sensors that are already in the body of a patient but have been disconnected from sensor electronics for a short amount of time, such as less than 2 hours.

In individuals using analyte sensors in non-hospital settings (e.g. diabetics using glucose sensors to manage their disease), relatively long sensor initialization and/or start-up periods are also problematical due to both the inconvenience to the user as well as the delayed receipt of information relating to user health. Because many diabetics do not have medical training, they may forgo optimal monitoring and modulation of blood glucose levels due to complexities associated with such management, for example, a two hour start-up period which can be an inconvenience in view of a patient's active daily routine. For these reasons, sensors and sensor systems that are designed to include elements and/or configurations of elements can reduce sensor initialization and/or start-up times in are highly desirable in situations where such sensors are operated by a diabetic patient without medical training because they facilitate the patient's convenient management of their disease, behavior which is shown to decrease the well known morbidity and mortality issues observed in individuals suffering from chronic diabetes.

While the analyte sensor and sensor systems disclosed herein are typically designed to be implantable within the body of a mammal, the inventions disclosed herein are not limited to any particular environment and can instead be used in a wide variety of contexts, for example for the analysis of most in vivo and in vitro liquid samples including biological fluids such as interstitial fluids, whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

In certain embodiments of the invention, distributed electrode configurations are used in methods designed to overcome problems with sensors and sensor systems that occur due to lack of hydration (e.g. slow start-up initialization times), fluid stagnation, a patient's immune response, or the like. For example, systems with such distributed electrode configurations are shown in U.S. Pat. No. 6,770,729, which is incorporated herein by reference.

In some sensor embodiments, the distributed electrodes are organized/disposed within a flex-circuit assembly (i.e. a circuitry assembly that utilizes flexible rather than rigid materials). Such flex-circuit assembly embodiments provide an interconnected assembly of elements (e.g. electrodes, electrical conduits, contact pads and the like) configured to facilitate wearer comfort (for example by reducing pad stiffness and wearer discomfort) as well as parameter measurement performance and are disclosed in more detail in U.S. patent application Ser. No. 12/184,046 (filed Jul. 31, 2008), which is hereby incorporated by reference.

Typically, the electrodes in a sensor are of a rectangular shape, i.e. have a longer side and a shorter side (including those of a rectangular shape, yet having rounded edges). In some embodiments of the invention, the electrode configuration is such that a longer side of at least one of the electrodes in a distributed electrode pattern is parallel to an longer side of at least one of the other electrodes in the distributed electrode pattern (and optionally all of the electrodes in the distributed electrode pattern). Example sensors are shown in U.S. patent application Ser. No. 12/184,046 (filed Jul. 31, 2008), incorporated herein by reference.

In some embodiments of the invention, an aperture is positioned on the cover layer so that a fluid comprising the analyte contacts the reference electrode, the working electrode and the counter electrode in a sequential manner so as to facilitate sensor hydration and/or sensor start-up or initialization. In some embodiments of the invention, the aperture is fully open, i.e. opens the electrodes to the external environment by having aperture edges that line up with or are below the electrodes in the sensor. An optimized profile is shown in U.S. patent application Ser. No. 12/184,046 (filed Jul. 31, 2008), incorporated herein by reference.

In certain embodiments of the invention, sensor systems that comprise wire electrodes are used in methods designed to overcome problems that can occur with implantable sensors and sensor systems due to lack of hydration (e.g. slow start-up initialization times) and/or fluid stagnation by enhancing the flexing and movement of the implanted components in a manner that enhances fluid flow and inhibit a gas bubble or a stagnating pool of fluid from remaining on top of or close to an electrode in a manner that compromises sensor function. In addition, embodiments of the invention that comprise a wire electrodes can be combined with certain complementary elements disclosed herein so as to further overcome problems that result from a lack of hydration, fluid stagnation, a patient's immune response, or the like (e.g. distributed electrode configurations, flex sensor assemblies, multiple electrode sensors, voltage pulsing methods etc.).

As discussed herein, the sensor may be directly connected to sensor electronics, which may be part of or separately connected (wirelessly or via or other direct connection) to a monitoring device that monitors the signals received from the sensor. Depending on the construction of the sensor device and/or monitor (whether separate or together with the sensor device), one or both of the sensor electronics and monitor may make calculations based on the signals sensed at the sensor to convert the signals to actual analyte measurements and to determine various characteristics of the data received. As discussed herein, a number of different characteristics may be used to help get a more accurate picture of the actual level of analyte in the patient. These characteristics can include current values at different time intervals, such as during relaxation of the curve, change in currents, change in total charge, and/or calculated relaxation parameters.

Embodiments of the invention include sensors and sensor systems having configurations of elements and/or architectures that optimize aspects of sensor function. For example, certain embodiments of the invention are constructed to include multiple and/or redundant elements such as multiple sets of sensors and/or sensor system elements such as multiple piercing members (e.g. needles) and/or a cannulas organized on an insertion apparatus for use at a patient's in vivo insertion site. For example, sensor sets may include dual piercing members as disclosed in U.S. patent application Ser. No. 13/008,723, filed Jan. 18, 2011, which is herein incorporated by reference.

In some embodiments of the invention, the first and second electrochemical sensors are operatively coupled to a sensor input capable of receiving signals from the first and second electrochemical sensors; and a processor coupled to the sensor input, wherein the processor is capable of characterizing one or more signals received from the first and second electrochemical sensors. Optionally, a pulsed voltage is used to obtain a signal from an electrode. In certain embodiments of the invention, the processor is capable of comparing a first signal received from a working electrode in response to a first working potential with a second signal received from a working electrode in response to a second working potential.

While embodiments of the invention can comprise one or two piercing members, optionally such sensor apparatuses can include 3 or 4 or 5 or more piercing members that are coupled to and extend from a base element and are operatively coupled to 3 or 4 or 5 or more electrochemical sensors (e.g. microneedle arrays, embodiments of which are disclosed for example in U.S. Pat. Nos. 7,291,497 and 7,027,478, and U.S. patent Application No. 20080015494, the contents of which are incorporated by reference). In addition, while embodiments of the invention typically include a base element that positions and supports the implanted sensors, in alternative embodiments of the invention, the plurality of sensors are not coupled to a base element.

As noted above, certain embodiments of the invention can use voltage switching as part of the sensing process. Embodiments of the invention can use voltage switching not only in the detection of interfering species and/or specific analyte concentrations but also to facilitate the hydration and/or initialization of various sensor embodiments of the invention. In particular, the time for initialization ("run-in") differs for different sensors and can take hours. Embodiments of the invention include a sensor initialization scheme involving high frequency initialization (switching of voltage potentials). In one illustrative embodiment, a triple initialization profile is used where the voltage of the sensor is switched between a first potential such as 0, 280, 535, 635 or 1.070 millivolts and a second potential such as 0, 280, 535, 635 or 1.070 millivolts over a period of 5, 10, 20, 30 or 45 seconds or 1, 5, 10 or 15 minutes. Certain voltage switching embodiments of the invention further use voltage pulsing in the detection of analyte signals. The number of pulses used in such embodiments of the invention is typically at least 2 and can be 3, 4, 5, 6, 7, 8, 9, 10, 15, 20 or more. Pulses can be for a predetermined period of time, for example 1, 3, 5, 7, 10, 15, 30, 45, 60, 90 or 120 seconds. One illustrative example of this comprises 6 pulses, each a few seconds long. By using such embodiments of the invention, the sensor run-in is greatly accelerated, a factor which optimizes a user's introduction and activation of the sensor. Certain of these methods can be adapted for use with similar methods known in the art (see, e.g. U.S. Pat. Nos. 5,320,725; 6,251,260 and U.S. Patent Application No. 2005/0161346, the content of which are incorporated by reference).

In some embodiments of the invention, a pulsed (e.g. produced or transmitted or modulated in short bursts or pulses) voltage is used to obtain a signal from one or more electrodes of the sensor. In related embodiments of the invention, the use of a pulsed current or the like is used. Such pulsing for example can be used to reduce/compensate for background current readings. Pulsing allows sensors to detect lower concentrations of glucose more efficiently, that there is a linear response to glucose switching, and that pulsing can be used to both decrease the background current and reduce the effect of interferants. To eliminate the possibility of the sensors in these studies having a variety of different voltage pulsed and/or voltage switched sensor embodiments are contemplated. In this context, sensor systems can include a processor in or separate from sensor electronics, where the processor includes software algorithms that control factors such as voltage output and/or working potential and/or pulsing and or switching and/or the time periods of such factors. Sensor systems can also include various hardware features designed to facilitate voltage pulsing, for example discharge circuit elements. In particular, in certain embodiments of the invention, high frequency switching can require a discharge circuit element so that layers discharge held charge (wherein the sensor layers analogous to a capacitor). One illustrative embodiment is sensor having two specific potential dedicated electrodes (e.g. at 280 mv and 535 mv) and is designed to obtain readings of both electrodes as sensor switches between them. In this context, it is known in art to take sensor reading at a wide range of potentials (see, e.g. U.S. Pat. Nos. 5,320,725, 6,251,260, 7,081,195 and Patent Application No. 2005/0161346). In one illustrative embodiment of the invention, a processor is used to observing signals obtained from one of two working electrodes in a sensor via a pulsed voltage and comparing it to the signal obtained from the second working electrode, wherein this second working electrode is not exposed to a pulsed voltage.

In certain embodiments of the invention, sensor systems that utilize voltage pulsing and/or switching as disclosed herein are used in methods designed to overcome problems that can occur with implantable sensors and sensor systems due to lack of hydration (e.g. slow start-up initialization times) and/or fluid stagnation by enhancing the ability of a fluid to flow around the implanted components in a manner that inhibits the likelihood of a gas bubble or a stagnating pool of fluid from forming and/or remaining on top of or close to an electrode in a manner that compromises sensor function. In addition, embodiments of the invention that utilize voltage pulsing and/or switching can be combined with certain complementary elements disclosed herein so as to further overcome problems that result from a lack of hydration, fluid stagnation, a patient's immune response, or the like (e.g. distributed electrode configurations, multiple electrode sensors, multiple sensor apparatuses having multiple implantation sites, etc.).

In embodiments of the invention, varied voltage is used, for example applying repeated cycles of step electrode potentials. The varied voltage results in a continuous mode of glucose sensing providing much more information during chronological glucose monitoring. Using a varying voltage scheme such as a stepped voltage scheme has many advantages. For example, its inherent self-correlation is quite large compared to a constant potential approach.

When step electrode potentials are used, for example each waveform cycle of signal relaxation response that is obtained contains a number of characteristic electrode current readings (Isigs). These readings change and relaxation times will directly correlate with glucose concentrations. Continuous repetition of such cycles results in a robust continuous glucose monitoring system. The characteristic signal responses, by correlating to glucose, also correlate with each other under normal conditions throughout any glucose changes. Thus, this method provides higher system reliability as compared to a fixed potential sensing mode, which only returns one characteristic electrode current reading during sensing. Changes in system self-correlation based on multiple electrode potentials can also be useful in identifying the presence of substances that may interfere with glucose response and tracking such as interferants. In embodiments of the invention, multiple electrode potentials are used, for example, stepped electrode potentials.

As discussed herein, methods such as voltage switching may be used to initialize the sensor prior to the time at which sensing data will be used to determine analyte readings. As such, there may be an initialization period prior to the sensor duration time period. In addition or alternatively, also as discussed herein, there may be a hydration period prior to the sensor duration time period.

Figure 9A:
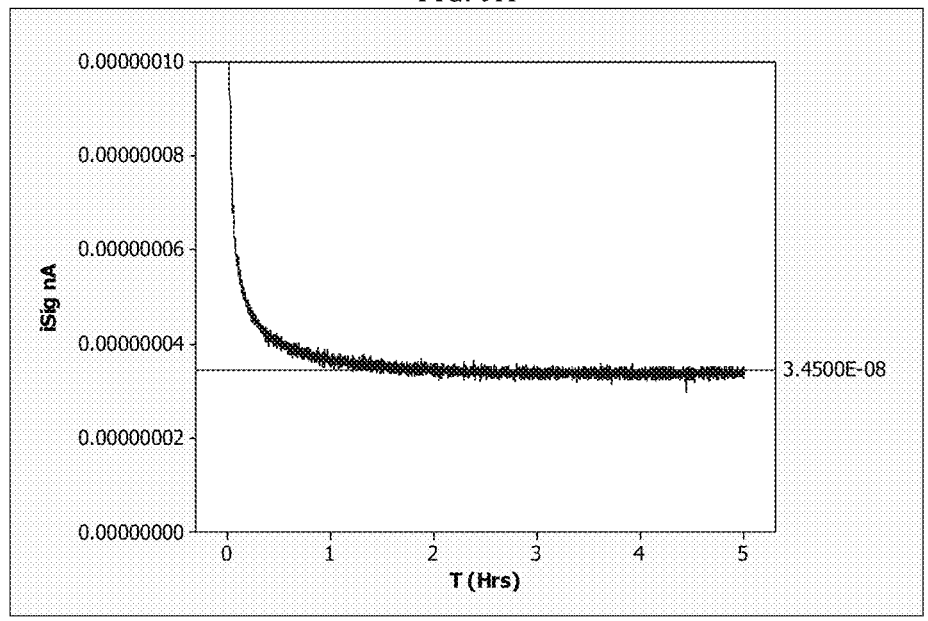
FIG. 9A provides a graph showing the signal response (iSig) when a sensor is reconnected to a processor after 2 hours of disconnection.

In some cases, the sensor needs to be disconnected from the sensor electronics for a period and then reconnected. For example, in hospitals, a sensor may need to be disconnected during certain operations or procedures. One such procedure is magnetic resonance imaging (MRI), which is not compatible with processors or sensor electronics. In such cases, the sensor is disconnected for a certain amount of time and then reconnected to the sensor electronics. Unfortunately, the prior art processes of initialization can take up to a couple of hours. During normal operation in certain embodiments, the sensor operates in an amperometric detection mode at a steady operation potential (e.g., 0.535 V) to provide a steady-state faradaic current response that corresponds to the glucose concentrations. In an event when the sensor needs to be disconnected and reconnected for a brief period of time, the sensor undergoes transient current response which is non-faradaic and does not truly correspond to actual glucose values. The typical response curve is shown in FIG. 9A, which shows the current response (iSig) in nA over a period of time. For an implanted sensor, this transient response can cause delayed start-up after reconnecting. The transient current response could last from several minutes to a couple of hours before the sensor is stabilized. The length of time for this transient current also depends on how long the sensor was disconnected.

Figure 9B:
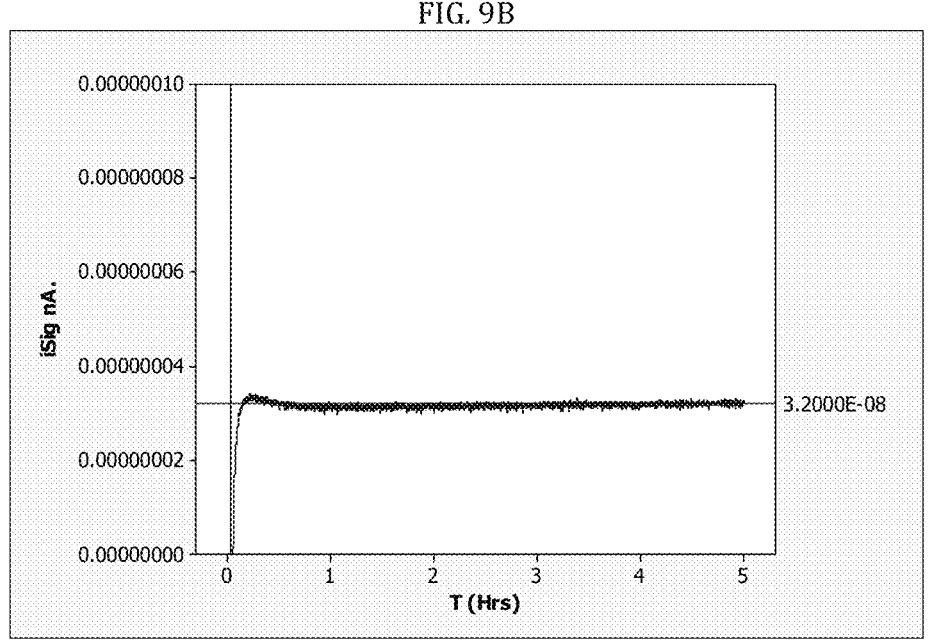
FIG. 9B provides a graph showing the signal response (iSig) when a sensor is reconnected to a processor after 2 hours of disconnection and initialized according to an embodiment of the present invention.

To minimize the delayed start-up upon reconnection of the sensor, embodiments of the present invention use a soft initialization method. In this soft initialization method, voltage steps or other variations are applied in sequences that will minimize the time to reach steady state current. The typical response curve after soft initialization is shown in FIG. 9B. As can be seen, and as discussed further herein, the time for the response to normalize is much less than without the soft initialization method.

In embodiments of the invention, a method is provided for detecting disconnection and reconnection of the sensor electronics processor to the sensor. Current output to the sensor electronics processor is measured. When the current output is below a disconnection threshold, an event of disconnection is determined. The threshold may be, for example, 0.6 nA. After a disconnection event, the current output level to the sensor electronics continues to be measured. When it rises above a reconnection threshold, an event of reconnection is determined. The threshold may be the same as the disconnection level or it may be smaller, for example, 0.4 nA. In embodiments of the invention, the threshold disconnection level may be any level up to about 1.0 µA.

When the events of disconnection and reconnection are measured, the amount of time of disconnection may also be measured. If this disconnection time falls within certain ranges, the system of the present invention may select a type of initialization. For example, there may be two or three disconnection time ranges. It is possible that there could me more disconnection time ranges if fourth, fifth, or more types of initializations are desired.

Typical embodiments of the invention comprise a method of initializing a sensor (typically an analyte sensor, such as a glucose sensor) by determining a disconnection time, wherein the disconnection time is the amount of time a sensor has been disconnected from sensor electronics. In such embodiments, an initialization protocol is then selected based on the disconnection time. In embodiments of the invention, the disconnection time can be characterized by determining if it falls within a selected time range. In some embodiments of the invention, time range can comprise times above and/or below a specific time point that a sensor has been disconnected from sensor electronics, for example, sensors having been disconnected from sensor electronics for at least 5, 10, 15, 30, 60, 90 or 120 minutes (e.g. a time range of 5 minutes to infinity etc.), or sensors having been disconnected from sensor electronics for less than 5, 10, 15, 30, 60, 90 or 120 minutes (e.g. a time range of 0-5 minutes etc.). In certain embodiments of the invention, time ranges can comprise windows of time that a sensor has been disconnected from sensor electronics, for example, sensors having been disconnected from sensor electronics from between 1-5 minutes, 1-10 minutes, 5-10 minutes, 5-15 minutes, 10-30 minutes, 10-60 minutes, 10-90 minutes or 10-120 minutes etc.

In typical embodiments of the invention, the initialization protocol is selected from the group consisting of: a first initialization scheme comprising a first series of voltage pulses and a second initialization scheme comprising a second series of voltage pulses, wherein the first initialization scheme is selected if the disconnection time falls within a first time range and the second initialization scheme is selected if the disconnection time falls within a second time range; and applying the selected initialization protocol to the sensor. The initialization protocol may further be selected from the group consisting of a third initialization scheme comprising the application of no voltage to the sensor, wherein the third initialization scheme is selected if the disconnection time is less than the first time range and the second time range. Alternatively, the third initialization scheme may be selected if the disconnection time falls within a third time range. There may be additional initialization schemes and time ranges as desired. In an example embodiment, the first initialization scheme is a hard initialization scheme, the second initialization scheme is a soft initialization scheme, and the third initialization scheme is a no voltage initialization scheme, all three of which are discussed herein.

As noted above, in embodiments of the present invention there are three disconnection time ranges, and three respective types of initialization. These three types of initialization include a hard initialization scheme, for those sensors disconnected for more than a certain amount of time, such as 2 hours, a soft initialization scheme, for those sensors disconnected less than that first amount of time but more than a smaller amount of time, such as 10 minutes, and a no voltage initialization scheme for those sensors disconnected less than the smaller amount of time. This allows for sensors having been disconnected long enough to need a complete, hard initialization, sensors that can be initialized using an intermediate, soft initialization, and sensors that really don't need an initialization because they've been disconnected for such a short period of time. In further embodiments, there might be only the hard and no voltage initiation schemes, or only hard and soft, or only soft and no voltage initialization.

Figure 4:
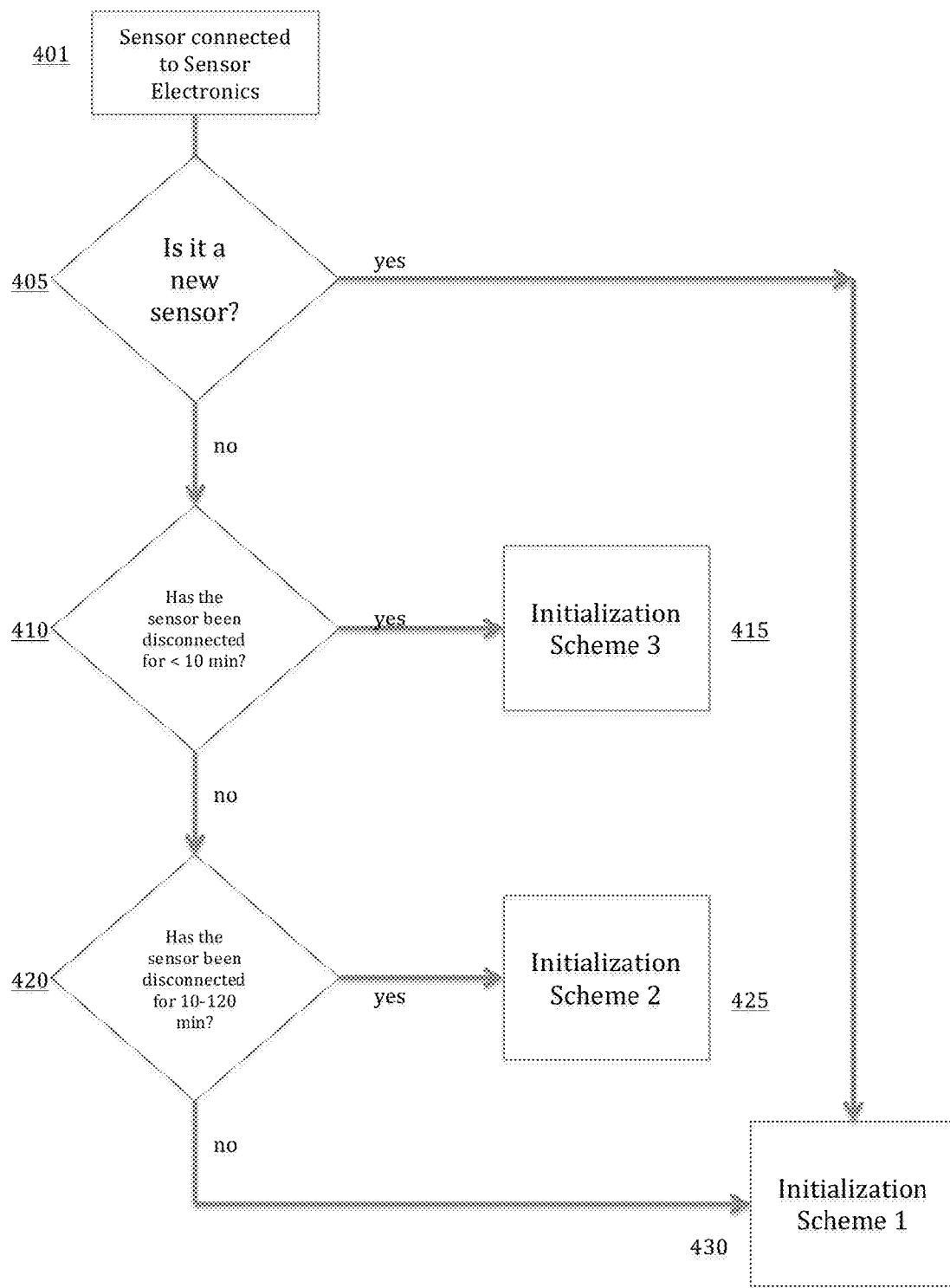
FIG. 4 provides a flow chart illustrating selection of an initialization scheme according to an embodiment of the invention.

In embodiments of the present invention, there are three disconnection time ranges, and three respective types of initialization. As shown in FIG. 4, when a sensor is connected to sensor electronics at step 401 the system determines whether the sensor is a new sensor or a reconnected sensor at step 405. If the sensor is a new sensor, the system goes to initialization scheme 1 at step 430 and FIG. 5. If the sensor is not a new sensor, the system determines whether the sensor disconnection time is within a certain range, for example less than 10 minutes, at step 410. If the sensor disconnection time is within that range, then initialization scheme 3 is selected at step 415 and FIG. 7. If the sensor disconnection time is not within that range, then it is determined whether the sensor disconnection time is within a second disconnection range, for example 10-120 minutes, at step 420. If the sensor disconnection time is within that range, then initialization scheme 2 is selected at step 425 and FIG. 6. If the sensor disconnection time is not within that range, then it will fall within the remaining range of time, for example greater than 120 minutes, and initialization scheme 1 is initialized at step 430 and FIG. 5.

Although a particular selection process is shown in FIG. 4, it is possible that the particular process could be different. For example, the disconnection time could be compared to a lookup table or it could be steps in a different order, however a programmer sees suitable to prepare the process such that one of three initialization schemes is selected based on the disconnection time ranges.

Figure 5:
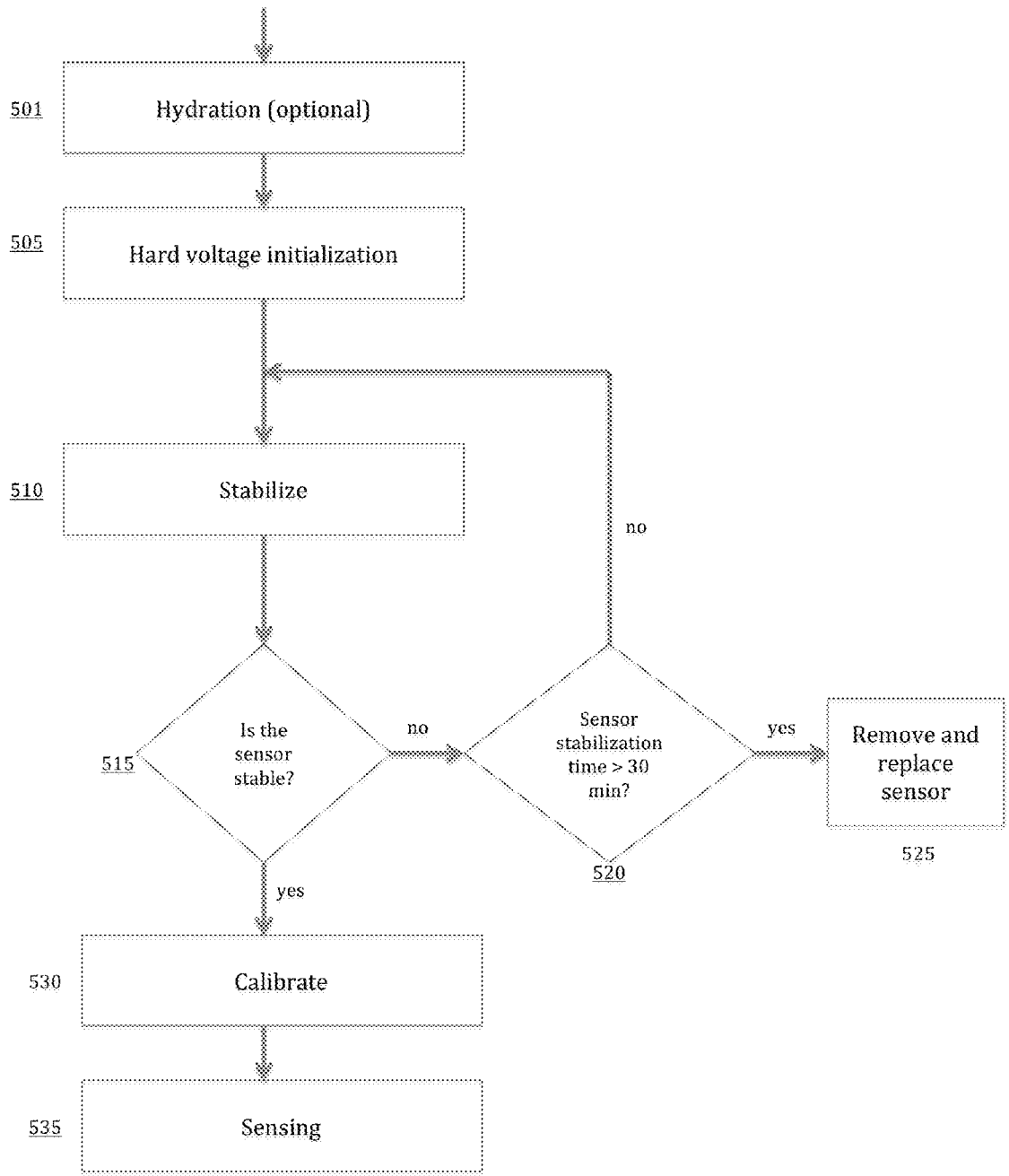
FIG. 5 provides a flow chart illustrating an initialization scheme according to an embodiment of the invention.
Figure 10:
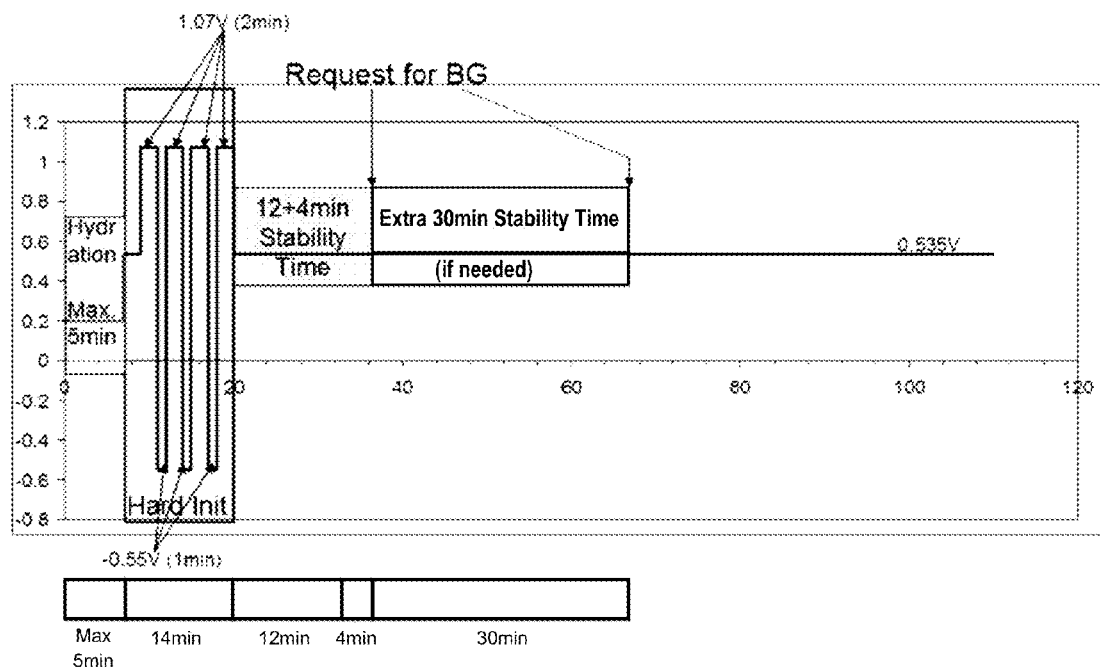
FIG. 10 provides a graphical illustration of an initialization scheme according to an embodiment of the invention FIG. 11 provides a graphical illustration of an initialization scheme according to an embodiment of the invention.

A sample hard initialization scheme, initialization scheme 1 is shown in FIG. 5. Under embodiments of the invention, a hard initialization is used for new sensors or when the sensor has been disconnected from the sensor electronics for greater than a certain amount of time. Initially, hydration of the sensor may be performed at step 501. Hydration techniques may be conventional techniques or other techniques described herein. After hydration, if performed, a hard voltage initialization is performed at step 505. The hard voltage initialization may be performed using voltage switching, pulsing, or stepping, as described herein. An example hard voltage initialization is shown in FIG. 10. After up to 5 minutes of hydration, a voltage switching scheme is employed until the minute mark. Thus, in the embodiment shown in FIG. 10, if 5 minutes of hydration is performed, 15 minutes of hard initialization voltage switching is performed, switching between 1.07V for 2 minutes and −0.55V for 1 minute. The particular embodiment in the figure is illustrative and different voltages and time periods could also be used. For example, additional voltages could be positive or negative 0, 280, 535, 585, 635 and 1.070 mV.

After the hard voltage initialization at 505, stabilization is performed at step 510. The stabilization may be performed by applying the operating voltage, for example 535 mV, for a certain amount of time, for example 16 minutes. At step 515, the system determines whether the sensor is stable. Metrics of glucose sensor signal stability are known in the art and described, for example, in WO/2011/163294. In some embodiments, sensor stability is determined, for example, by determining whether the sensor exhibits a fixed current profile in the presence of unchanging glucose concentrations. In some embodiments, sensor stability is determined, for example, by determining whether the sensor has achieved 90% of a maximum unchanged signal in the presence of unchanging glucose concentrations. In some embodiments, sensor stability is determined, for example, by determining whether the sensor exhibits limiting current in the presence of unchanging glucose concentrations.

If the sensor is not stable (e.g. does not exhibits a fixed current profile in the presence of unchanging glucose concentrations), the system performs additional stabilization until a maximum stabilization time or a maximum additional stabilization time is reached (e.g. a preselected time for stabilizing the sensor such as 15, 30, 45, 60, 90, 120, 180 or more minutes). In the embodiment shown in FIG. 5, the system determines whether there has been stabilization for less than a maximum stabilization time, such as 30 minutes, at step 515. If not, then additional stabilization is performed at step 510. The additional stabilization can be for the same amount of time as the original stabilization time or a different amount of time. For example, it might be useful to have a smaller secondary stabilization time because the sensor has already been stabilizing for a period of time and may just need a short amount of time to stabilize. Also, the system could be set up to have a series of small stabilization times, such as 1 or 5 minutes followed by stabilization checks. In other embodiments, the stabilization check could be going on during the stabilization period such that there is not a loop type stabilization process but instead a continuous stabilization with stabilization checks until stabilization is reached. If the sensor does not become stabilized after a maximum amount of time, the sensor is not useable and should be removed and replaced. This is shown in FIG. 5 as step 525. As shown in FIG. 5, if the sensor is stable, it is calibrated at step 530. Calibration may be performed using a blood glucose meter as described in U.S. patent application Ser. No. 09/334,996, filed Jun. 17, 1999, entitled "Characteristic Monitor With A Characteristic Meter and Method of Using the Same," which is incorporated by reference herein, and U.S. patent application Ser. No. 11/931,866, filed Oct. 31, 2007, entitled "Modified Sensor Calibration Algorithm," which is also incorporated by reference herein or by other calibration methods. Traditional calibration methods use a real time glucose value taken by blood glucose meter using the traditional finger-prick method (and analysis of the blood taken therefrom) and using that real value to calibrate the values being obtained by the sensor inside the body and related sensor electronics. These methods or other calibration methods may be used with the embodiments discussed herein.

After calibration, sensing may begin at step 535. It is further possible, although it may not be as efficient, that there may be a stabilization period with no check whether or not the sensor is stable at the end of the stabilization period.

Figure 6:
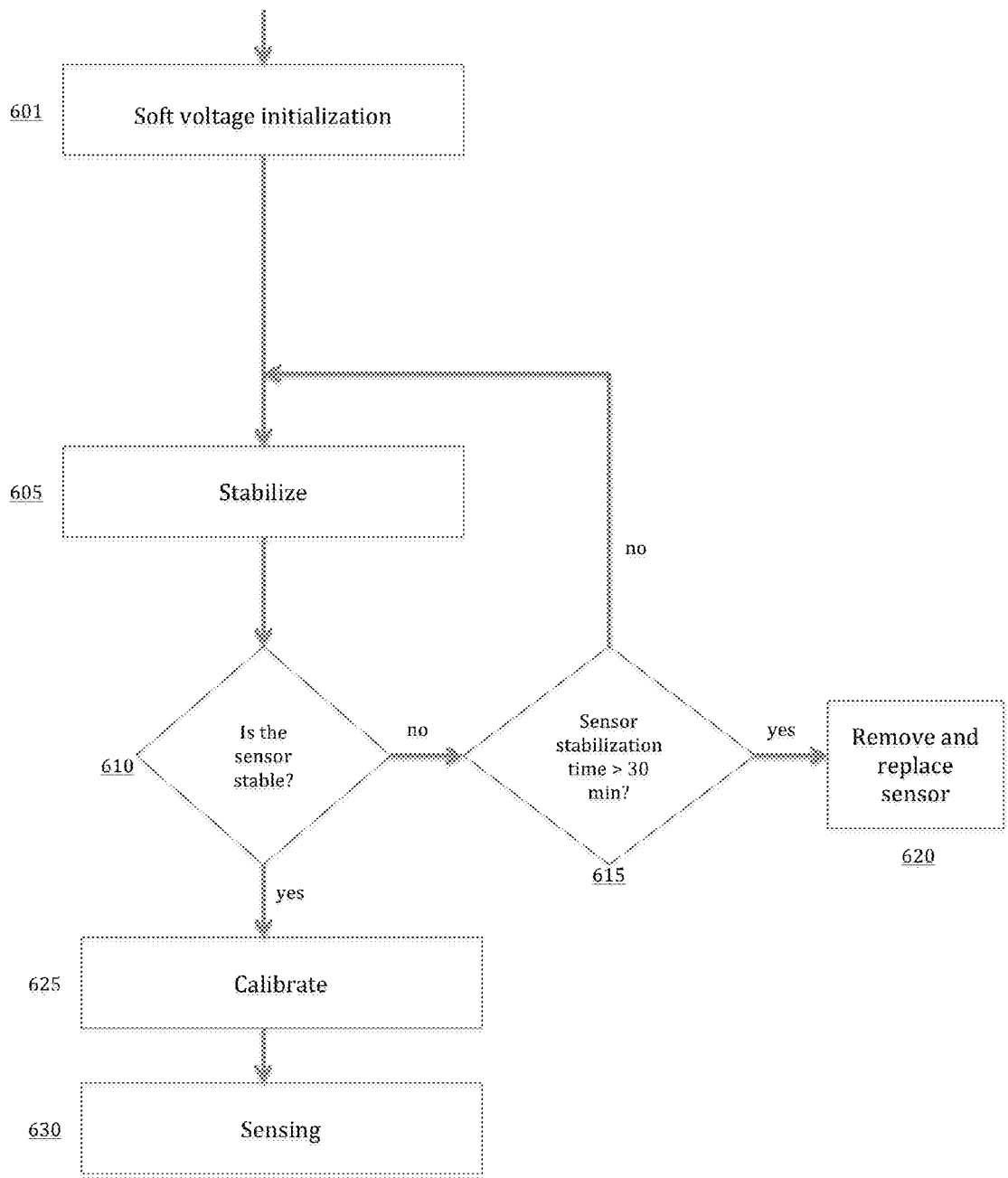
FIG. 6 provides a flow chart illustrating an initialization scheme according to an embodiment of the invention.

A sample soft voltage initialization scheme, initialization scheme 2, is shown in FIG. 6. The soft initialization is used for sensors that have been previously connected to sensor electronics and are being reconnected. In certain embodiments, such as shown in FIG. 4, the soft initialization is not used for sensors that have been disconnected for more than a predetermined amount of time, such as 2 hours. However, it is possible that a soft initialization may be useful for any disconnected sensor that is being reconnected, without a maximum disconnection period of time. With or without the maximum disconnection time, there may also be a minimum disconnection time for using the soft initialization, such as 10 minutes.

Figure 8A:
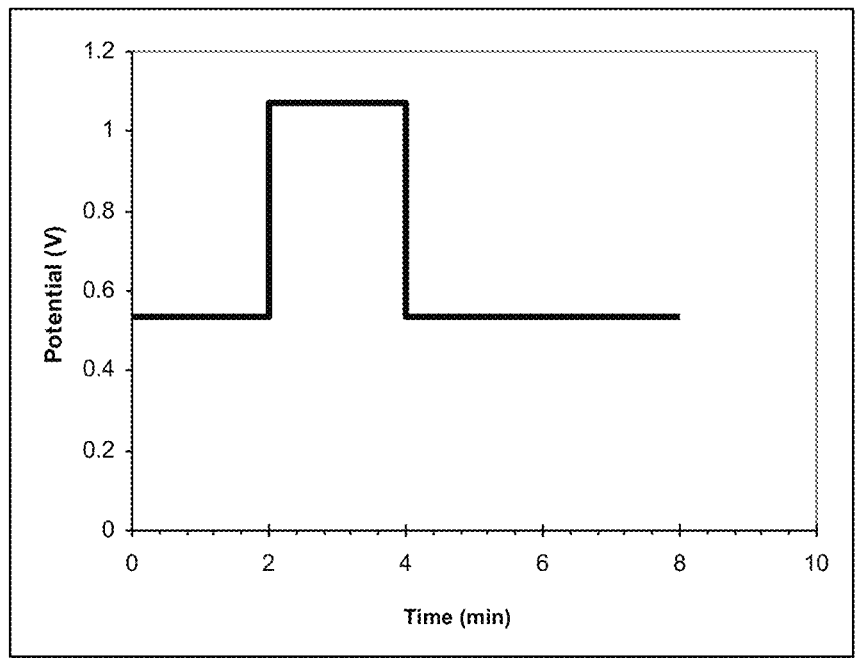
FIG. 8A provides a graph showing the potential (V) versus time (s) according to one embodiment of the present invention.
Figure 8B:
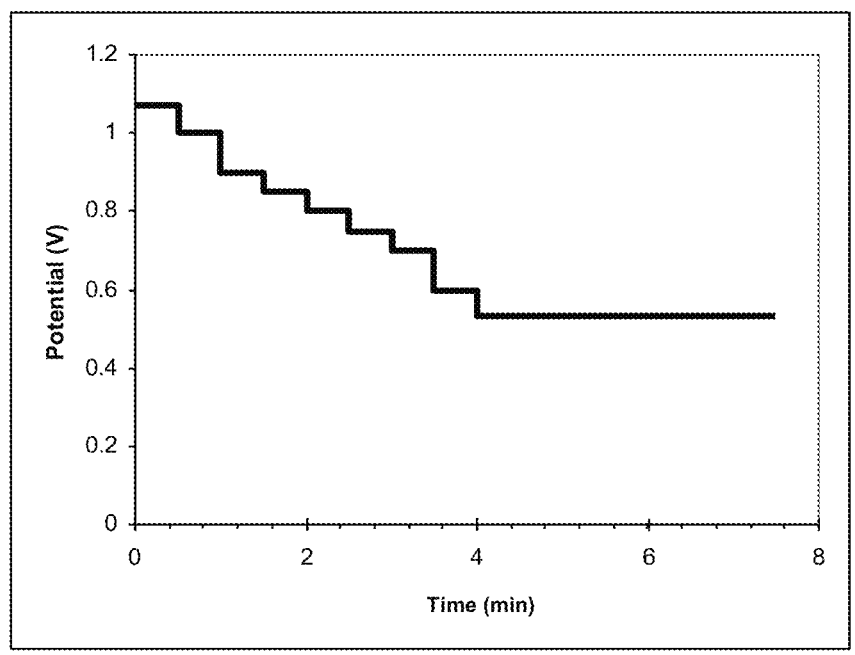
FIG. 8B provides a graph showing the potential (V) versus time (s) according to one embodiment of the present invention.

In the embodiment shown in FIG. 6, when initialization scheme 2 is selected, the soft voltage initialization is applied at step 601. It is generally not necessary to include a hydration step prior to the soft voltage initialization, because the sensor should remain inside a user's body. However, it is possible to do so if desired, for example if for some reason the user removes a replaceable sensor from the body and then replaces it prior to reconnection. In embodiments of the invention, the soft initialization procedure involves a series of potential steps to the sensor using a processor. In certain embodiments, the number of potential steps could range from 2 to 20 steps. It is also possible to have more of a voltage switching or pulsing type initialization. In some embodiments of the invention, there may be more than 20 steps or there may be several steps repeated as a sequence (e.g., V1, V2, V3, V1, V2, V3, etc., where V1, V2 and V3 each are stepped voltages). In certain embodiments, the sequence of steps lasts between about 1 and about 10 minutes. It's possible to have more or less time if desired, such as 8 minutes. One example of the soft voltage initialization is shown in FIG. 8A. As can be seen, a potential of 0.535V is applied for 2 minutes. Then a potential of 1.07V is applied for 2 minutes, after which the operating potential of 0.535V can be applied. Another example of the soft voltage initialization is shown in FIG. 8B, where a series of 8 potential steps are used to gradually step down from an initial potential of 1.07V to the operating potential of 0.535V.

FIGS. 9A and 9B show the difference in response time with and without a soft initialization according to an embodiment of the present invention. FIG. 9A shows the signal response (iSig) of the sensor when the sensor is re-connected to the processor and sensor electronics after 2 hours of disconnection without any soft initialization. The start-up time (i.e., the time to reach 90% of the expected response) is over 60 minutes long. FIG. 9B shows the signal response when the sensor is reconnected to the processor after 2 hours of disconnect using the soft initialization shown in FIG. 8A. In the case in FIG. 9B, the start up time is less than 30 minutes, showing that the time can be greatly reduced even using a simple soft initialization method.

In alternate embodiments, other methods of hard voltage initialization for a sensor may be used, including those discussed herein and in U.S. Pat. Nos. 5,320,725; 6,251,260 and U.S. Patent Application No. 2005/0161346, the content of which are incorporated by reference.

Figure 11:
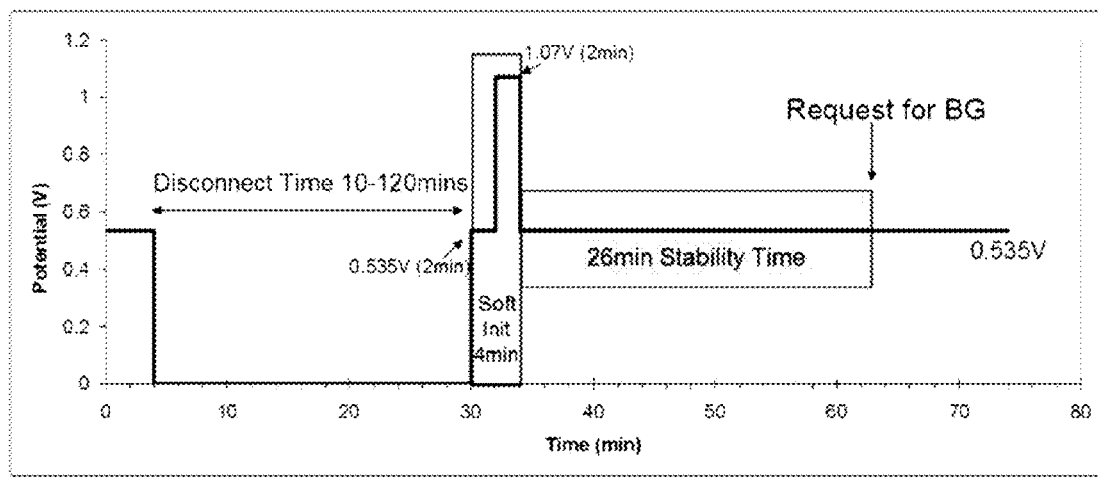
Figure 14:
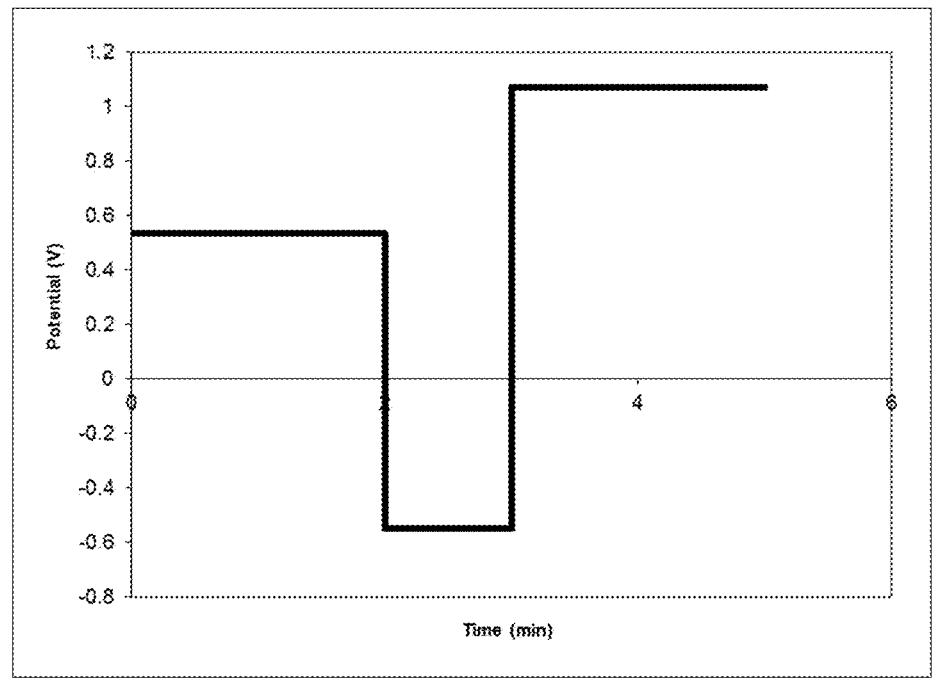
FIG. 14 is a graphical illustration of an initialization scheme according to an embodiment of the invention.
Figure 15:
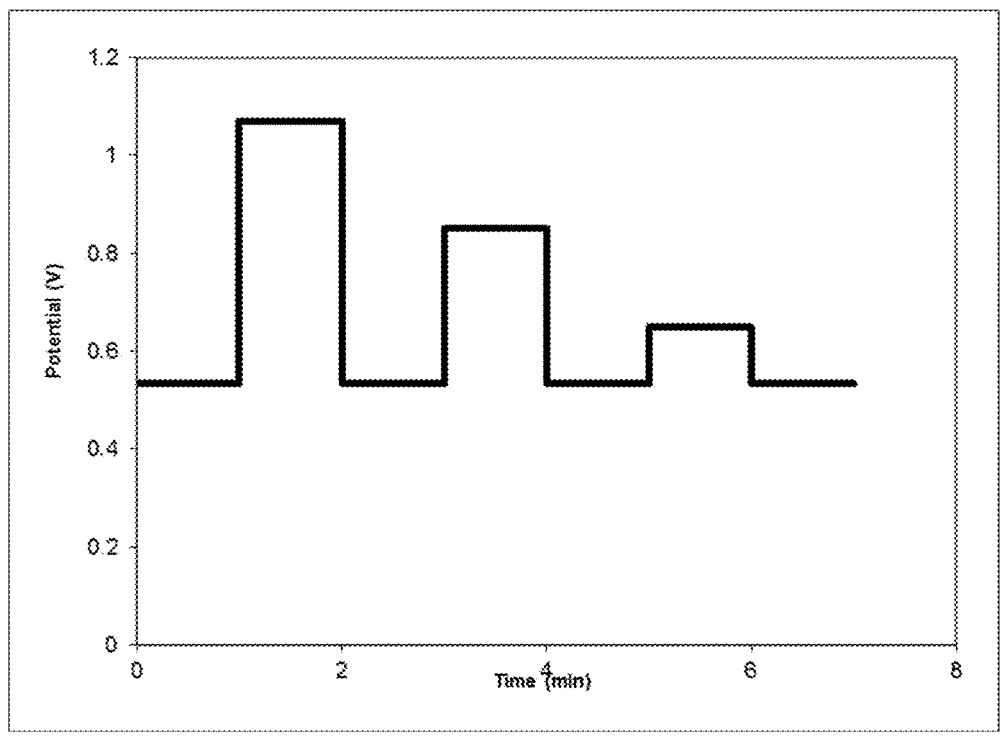
FIG. 15 is a graphical illustration of an initialization scheme according to an embodiment of the invention.
Figure 16:
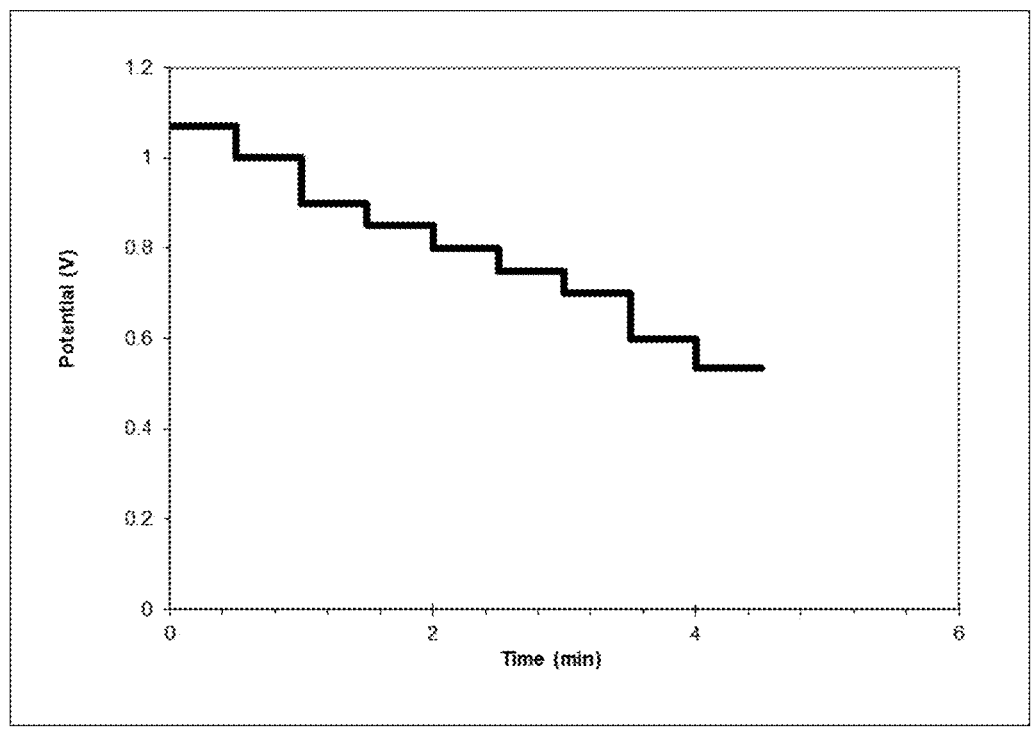
FIG. 16 is a graphical illustration of an initialization scheme according to an embodiment of the invention.
Figure 17:
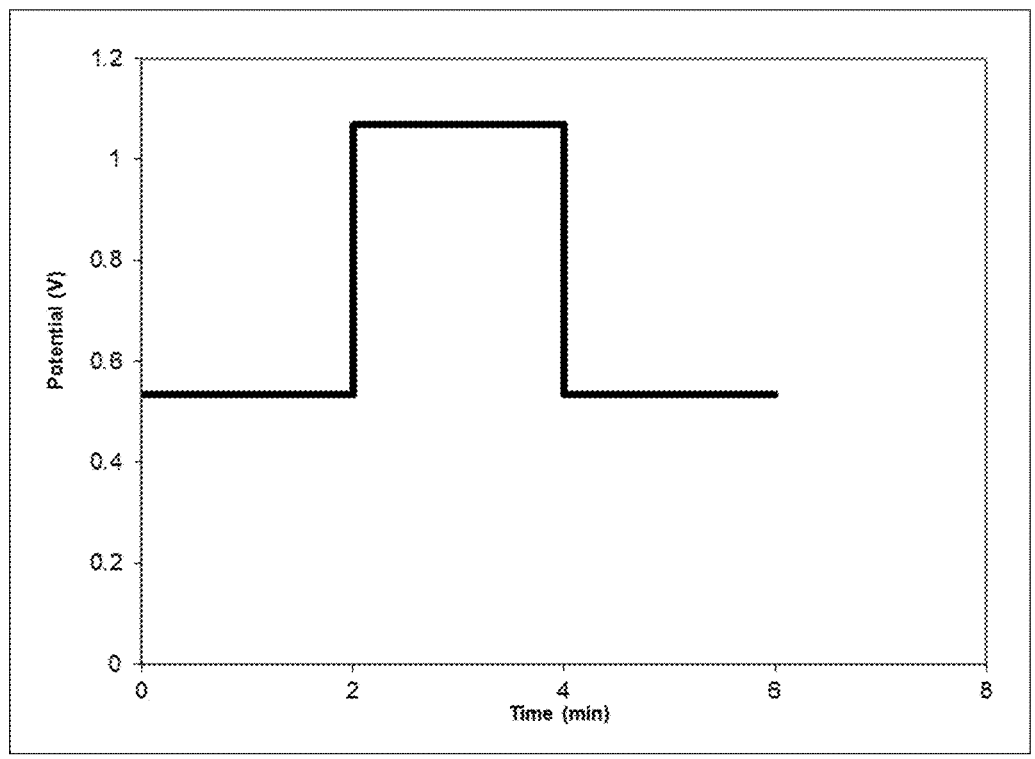
FIG. 17 is a graphical illustration of an initialization scheme according to an embodiment of the invention.

A sample soft initialization is shown in FIG. 11. In the embodiment shown in FIG. 11, the sensor is disconnected for between 10 and 120 minutes. When reconnected, the soft initialization starts with 2 minutes of 0.535V potential and then 2 minutes of 1.07V. The system them starts the operating voltage of 0.535V. The particular embodiment in the figure is illustrative and different voltages and time periods could also be used. Some additional examples are shown in FIG. 14-17. FIG. 14 shows a potential step of 0.535V for 2 minutes, a potential step of −0.55V for 1 minute, and a potential step of 1.07V for 2 minutes, which are then followed by operating potential, e.g. at 0.535V. FIG. 15 shows a step potential sequence of 0.535V for 1 minute, 1.07V for one minute, 0.535V for 1 minute, 0.85V for 1 minute, 0.535V for 1 minute, and 0.65V for 1 minute, followed by operating potential, e.g. at 0.535V. FIG. 16 shows a series of 8 potential steps that gradually steps down the voltage from 1.07V to an operation potential of 0.535V. FIG. 17 shows a potential step of 0.535V for 2 minutes then 1.07V for 2 minutes followed by operating voltage of 0.535V.

Figure 18:
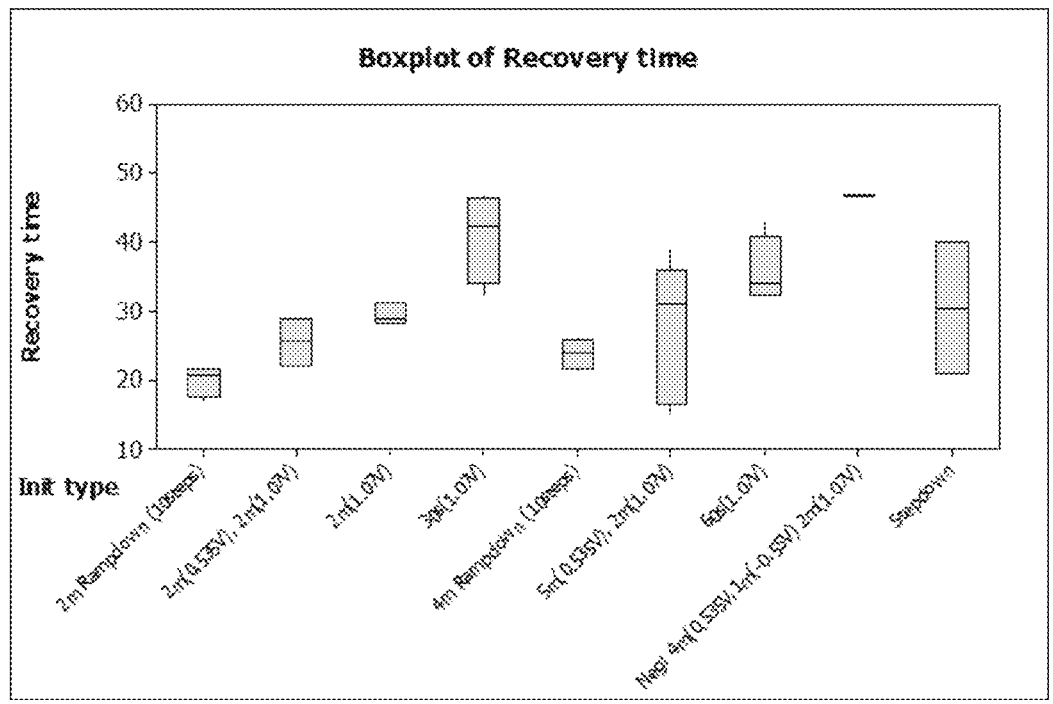
FIG. 18 is a graph showing a boxplot of recovery time for certain initialization schemes according to the present invention.
Figure 19:
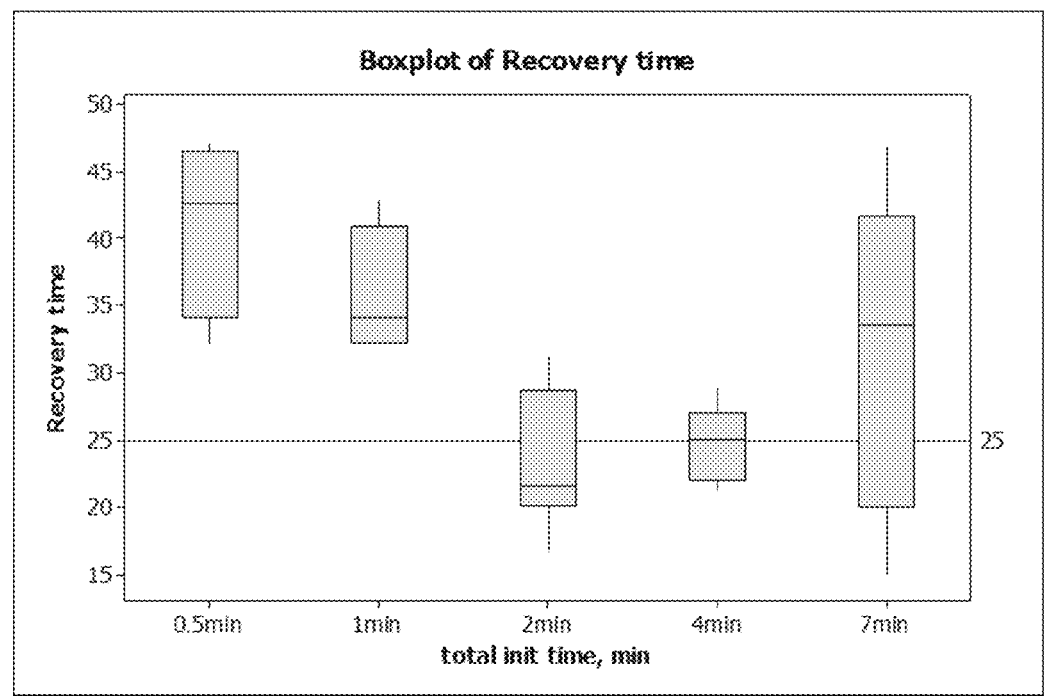
FIG. 19 is a graph showing a boxplot of recovery time based on the amount of time in an initialization scheme of the present invention.
Figure 20:
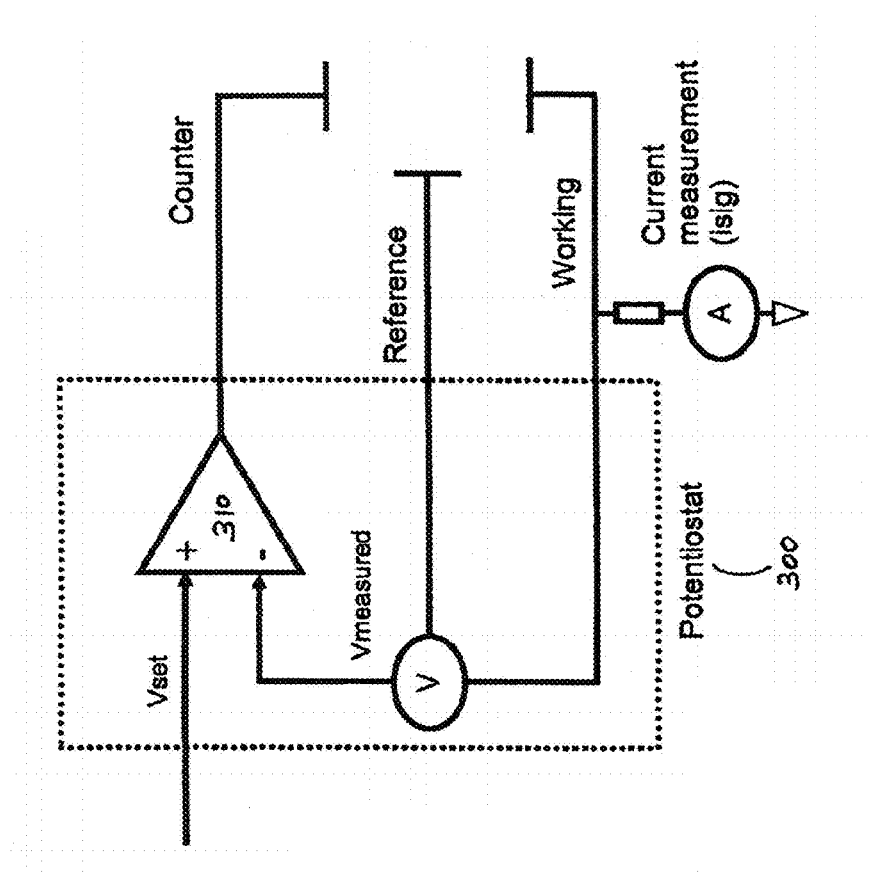
FIG. 20 shows a schematic of a potentiostat that may be used to measure current according to embodiments of the present invention.

FIGS. 18 and 19 show boxplots of recovery time, which in those FIGS. is defined as the time for the sensor to reach 90% of limiting current, for certain soft initialization schemes. In FIG. 18, the schemes are 2 minute rampdown with 10 steps (1801), 2 minutes at 0.535V and 2 minutes at 1.07V (1802), 2 minutes at 1.07V (1803), 30 seconds at 1.07V (1804), 4 minute rampdown with 10 steps (1805), 5 minutes at 0.535V and 2 minutes at 1.07V (1806), 60 seconds at 1.07V (1807), 4 minutes at 0.535V and 1 minute at −0.55V and 2 minutes at 1.07V (1808), and a stepdown scheme (1809). In FIG. 19, a boxplot is shown of the sensor recovery time based on the time of soft initialization, regardless of the soft initialization sequence used.

Continuing with FIG. 6, after the soft voltage initialization is applied at step, stabilization is performed at step 605. The stabilization may be performed by applying the operating voltage, for example 535 mV, for a certain amount of time, for example 10, 16, 20, or 26 minutes. At step 610, the system determines whether the sensor is stable. If the sensor is not stable, the system performs additional stabilization until a maximum stabilization time or a maximum additional stabilization time is reached. In the embodiment shown in FIG. 6, the system determines whether there has been stabilization for less than a maximum stabilization time, such as 30 minutes, at step 615. If not, then additional stabilization is performed at step 605. As with initialization scheme 1, the additional stabilization can be for the same amount of time as the original stabilization time or a different amount of time. The system could be set up to have a series of small stabilization times, such as 1 or 5 minutes followed by stabilization checks. In other embodiments, the stabilization check could be going on during the stabilization period such that there is not a loop type stabilization process but instead a continuous stabilization with stabilization checks until stabilization is reached. If the sensor does not become stabilized after a maximum amount of time, the sensor is not useable and should be removed and replaced. This is shown in FIG. 6 as step 620. As shown in FIG. 6, if the sensor is stable, it is calibrated at step 625. Calibration may be performed using a blood glucose meter as discussed above or by other calibration methods. After calibration, sensing may begin at step 630.

Figure 7:
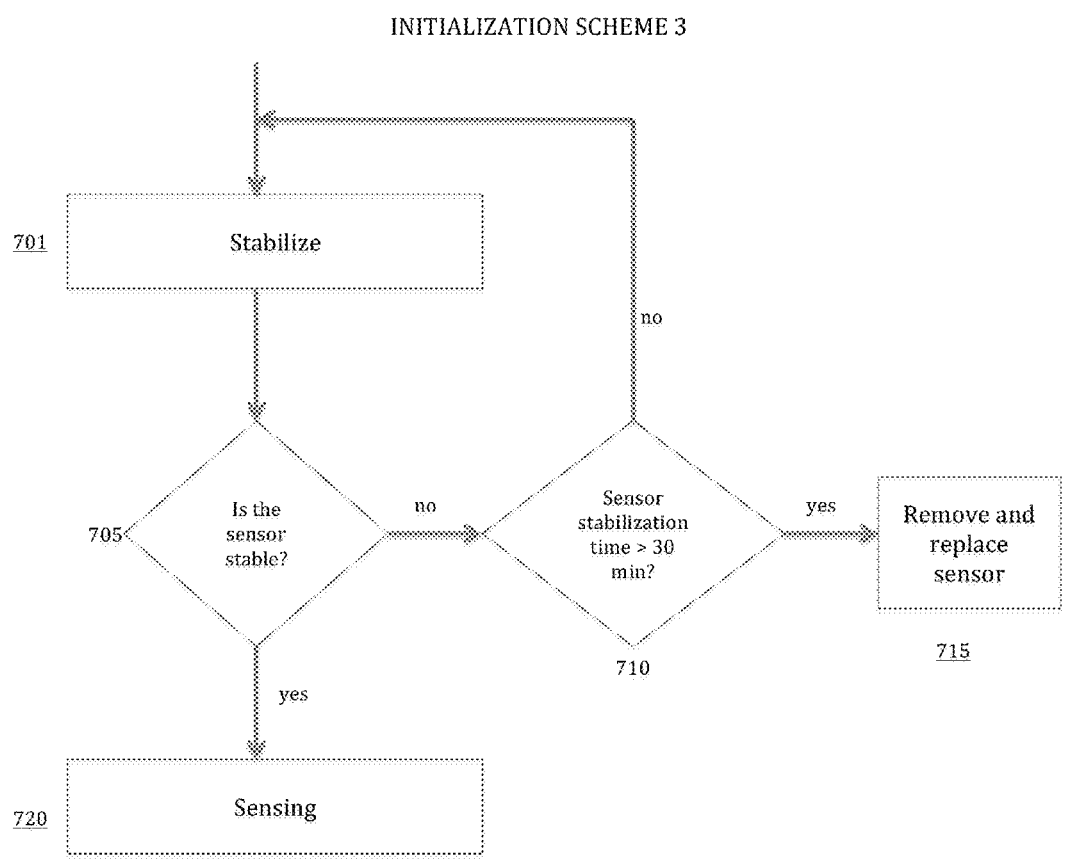
FIG. 7 provides a flow chart illustrating an initialization scheme according to an embodiment of the invention.
Figure 12:
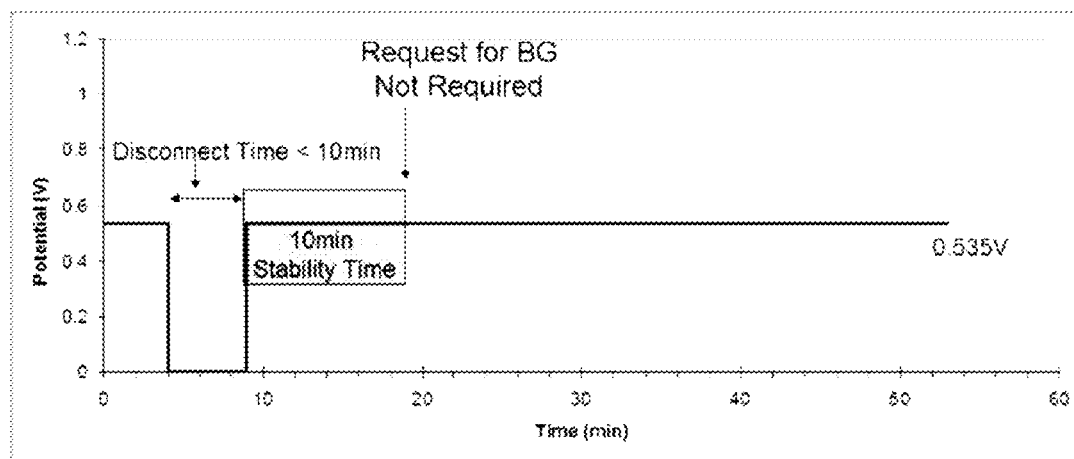
FIG. 12 provides a graphical illustration of an initialization scheme according to an embodiment of the invention.

A third scheme, initialization scheme 3, is shown in FIG. 7. In certain embodiments, it may be desired that sensors disconnected for a short period of time not be subjected to a new initialization, as this limited period of disconnection is insufficient for the sensor to need any initialization. A sample graph of initialization scheme 3 is shown in FIG. 12. In FIG. 12, the sensor has been disconnected for less than 10 minutes, so the system merely applies the operating voltage of 0.535V for a stabilization period of 10 minutes before moving on to sensing at the operating voltage. It is possible that this stability time be more or less, depending on how long of a stabilization period is desired. In some embodiments of the invention, as with initialization scheme 1 and 2, there may be a stabilization check. As shown in FIG. 7, a sensor that has fallen within the proper disconnection time range is stabilized at step 701. The stabilization may be performed by applying the operating voltage, for example 535 mV, for a certain amount of time, for example 10 minutes. Other time ranges could be employed, such as 16, 20 or 26 minutes. At step 705, the system determines whether the sensor is stable. If the sensor is not stable, the system performs additional stabilization until a maximum stabilization time or a maximum additional stabilization time is reached. In the embodiment shown in FIG. 7, the system determines whether there has been stabilization for less than a maximum stabilization time, such as 30 minutes, at step 710. If not, then additional stabilization is performed at step 701. The additional stabilization can be for the same amount of time as the original stabilization time or a different amount of time. As with the other initialization schemes, the system could be set up to have a series of small stabilization times, such as 1 or 5 minutes followed by stabilization checks. In other embodiments, the stabilization check could be going on during the stabilization period such that there is not a loop type stabilization process but instead a continuous stabilization with stabilization checks until a stabilization is reached. If the sensor does not become stabilized after a maximum amount of time, the sensor is not useable and should be removed and replaced. This is shown in FIG. 7 as step 715. In embodiments of the invention, no calibration is required for sensors falling under this initialization scheme, although it is of course possible to recalibrate if desired. Thus, sensing begins at step 720.

In some embodiments of the invention, the methods can further comprise applying a stabilization voltage to the sensor (e.g. a voltage designed to enhance sensor stability), for example after applying the selected initialization voltage, for a first stabilization time. The method may further include determining whether the sensor is stable after applying the first stabilization voltage; and if the sensor is not stable, applying a second stabilization voltage to the sensor for a second stabilization time. Example stabilization time periods include times less than forty minutes, such as 10, 16, 20, and 26 minutes, or 30 minutes. The second stabilization time may be the same or different than the first stabilization time.

Figure 13:
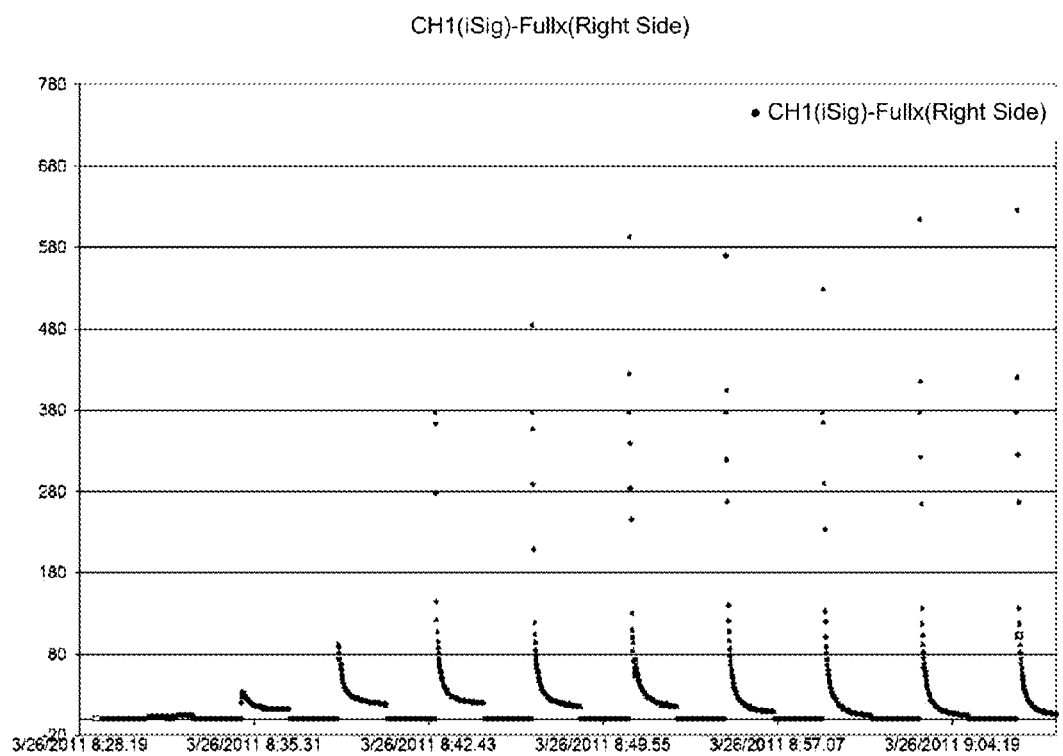
FIG. 13 is a graphical illustration of a hydration scheme according to an embodiment of the invention.

Some embodiments of the invention comprise an improved method of detecting and/or facilitating sensor hydration. For detection of hydration (e.g. the level or degree of implanted sensor hydration), voltage pulses are applied to the sensor immediately after insertion of the sensor and prior to sensor initialization using the sensor processor. The response (iSig) to this voltage pulse will be used for detection of hydration. In one embodiment, a pre-initialization voltage pulse scheme for detecting hydration is a set of two alternating voltages, such as 0.0V and 0.2V. Other potential voltages could be used, for example alternating voltages between 0.0V and a second voltage of between 0.1V and 0.535V. The sensor response (iSig) is recorded at a high sampling rate, such as every 1 second. The sensor is considered hydrated when the response to the voltage pulse is above a certain hydration threshold, such as 100 nA. Once the sensor is considered hydrated, the sensor undergoes initialization. If the threshold is not met after a certain amount of time, for example 5 minutes or up to about 20 minutes, the sensor will be considered not ready and will not go initialization. Instead, more similar pulses, which may be the same as the original pulses, are applied until the threshold is met. There may be a maximum hydration time period after which the sensor will be considered non-functioning and should be removed and replaced by a new sensor. FIG. 13 is an example graph showing the sensor response during hydration detection according to the embodiment shown above.

Some embodiments of the invention include detecting hydration of the sensor prior to applying the selected initiation protocol, wherein detecting hydration includes applying a series of hydration pulses (voltages selected to detect or facilitate sensor hydration) to the sensor for a first hydration time; recording the current response of the sensor during application of the series of hydration pulses; and comparing the current response to a predetermined hydration threshold. Application of the series of hydration pulses may be terminated if the current response reaches or exceeds the predetermined hydration threshold. Detecting hydration may further include applying a second series of hydration pulses to the sensor for a second hydration time if the current response does not reach the predetermined hydration threshold during the first predetermined hydration time. The predetermined hydration threshold may be 100 nA or 50 nA, for example. Example hydration pulses may be a series of 0 V and 2 V pulses, for example for 20 seconds or 2 minutes each.

The hydration detection described above may be used in combination with other methods, for the same or different sensors. For example, in some methods where more than one sensor is used, the hydration detection described above may be used with respect to one sensor and a different hydration detection may be used with respect to the other sensor. The sensors should become hydrated at roughly the same time, so this would serve as a check to make sure that they hydration detection methods are all correlating properly.

One example of another method to determine hydration includes using a processor that detects whether a sensor is sufficiently hydrated for analyte detection comprising a computer usable media including at least one computer program embedded therein that is capable of calculating an impedance value; and comparing the impedance value against a threshold to determine if the sensor is sufficiently hydrated for analyte detection. In related methods, detecting whether a sensor is sufficiently hydrated for analyte detection includes comprising calculating an open circuit potential value between at least two electrodes of the sensor and comparing the open circuit potential value against a threshold to determine if the sensor sufficiently hydrated for analyte detection. Typically, the open circuit potential value is the impedance value (and optionally this value is an approximation of a sum of polarization resistance and solution resistance). Optionally, the open circuit potential value is compared against an another threshold to determine if the sensor sufficiently hydrated for analyte detection. This can solve problems that occur when a user attempts to initialize a sensor that is not fully hydrated (e.g. compromising the accuracy and/or lifetime of the sensor).

Some embodiments of the invention include a fuse element that can be triggered after a predetermined period of time or event so as to interrupt a flow of electrical current within the apparatus (i.e. so as to disable the sensor), as disclosed in U.S. patent application Ser. No. 12/184,046 (filed Jul. 31, 2008), which is herein incorporated by reference.

In some embodiments of the invention, a processor is capable of comparing a first signal received from a working electrode in response to a first working potential with a second signal received from a working electrode in response to a second working potential, wherein the comparison of the first and second signals at the first and second working potentials can be used to identify a signal generated by an interfering compound. These methods are further discussed in U.S. application Ser. No. 12/184,046 (filed Jul. 31, 2008), which is herein incorporated by reference.

Certain sensor embodiments switch between a high potential to a low potential (e.g. with a frequency of less than 3, 2 or 1 seconds). In such embodiments, a sensor may not discharge, with for example sensor elements acting as a sort of capacitor. In this context, some embodiments of the invention can include a circuit discharge element that facilitates sensor circuit discharge (e.g. if discharge is not sufficient to reach a specific potential such as 535 millivolts). A variety of such circuit discharge elements known in the art can be adapted for use with sensor embodiments of the invention (see, e.g. U.S. Pat. Nos. 4,114,627; 4,373,531; 4,858,610; 4,991,583; and 5,170,806, 5,486,201, 6,661,275 and U.S. Patent Application No. 20060195148). Optionally for example, a sensor charge can be removed by connecting it through a discharging switch element, and optionally a discharging resistor element.

Sensors of the invention can also be incorporated in to a wide variety of medical systems known in the art. Sensors of the invention can be used, for example, in a closed loop infusion systems designed to control the rate that medication is infused into the body of a user. Such a closed loop infusion system can include a sensor and an associated meter which generates an input to a controller which in turn operates a delivery system (e.g. one that calculates a dose to be delivered by a medication infusion pump). In such contexts, the meter associated with the sensor may also transmit commands to, and be used to remotely control, the delivery system. Typically, the sensor is a subcutaneous sensor in contact with interstitial fluid to monitor the glucose concentration in the body of the user, and the liquid infused by the delivery system into the body of the user includes insulin. Illustrative systems are disclosed for example in U.S. Pat. Nos. 6,558,351 and 6,551,276; PCT Application Nos. US99/21703 and US99/22993; as well as WO 2004/008956 and WO 2004/009161, all of which are incorporated herein by reference.

A number of articles, U.S. patents and patent application describe the state of the art with the common methods and materials disclosed herein and further describe various elements (and methods for their manufacture) that can be used in the sensor designs disclosed herein. These include for example, U.S. Pat. Nos. 6,413,393; 6,368,274; 5,786,439; 5,777,060; 5,391,250; 5,390,671; 5,165,407, 4,890,620, 5,390,671, 5,390,691, 5,391,250, 5,482,473, 5,299,571, 5,568,806; United States Patent Application 20020090738; as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

Typical sensors for monitoring glucose concentration of diabetics are further described in Shichiri, et al.: "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al.: "In Vivo Measurement of Subcutaneous Glucose Concentrations with an Enzymatic Glucose Sensor and a Wick Method," Klin. Wochenschr. 67:491-495 (1989); and Pickup, et al.: "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

Various publication citations are referenced throughout the specification. In addition, certain text from related art is reproduced herein to more clearly delineate the various embodiments of the invention. The disclosures of all citations in the specification are expressly incorporated herein by reference.

What is claimed is:

1. A method of initializing a sensor, comprising:
   determining a disconnection time, wherein the disconnection time is the amount of time a sensor has been disconnected from sensor electronics,
      wherein the sensor is an analyte sensor,
   selecting an initialization protocol based on the disconnection time, the initialization protocol selected from the group consisting of:
      a first initialization scheme comprising a first series of voltage pulses and a second initialization scheme comprising a second series of voltage pulses,
   wherein the first initialization scheme is selected if the disconnection time falls within a first time range and the second initialization scheme is selected if the disconnection time falls within a second time range; and
   applying the selected initialization protocol to the sensor.

2. The method of claim 1, wherein the initialization protocol is selected from the group further consisting of a third initialization scheme comprising the application of no voltage to the sensor, wherein the third initialization scheme is selected if the disconnection time is less than the first time range and the second time range.

3. The method of claim 1, further comprising applying a first stabilization voltage to the sensor, after applying the selected initialization voltage, for a first stabilization time.

4. The method of claim 3, further comprising:
   determining whether the sensor is stable after applying the first stabilization voltage; and
   if the sensor is not stable, applying a second stabilization voltage to the sensor for a second stabilization time.

5. The method of claim 4, further comprising calibrating the sensor if the sensor is stable.

6. The method of claim 5, wherein calibrating the sensor includes measuring blood glucose using a blood glucose meter.

7. The method of claim 5, wherein calibration of the sensor is only performed if the disconnection time falls within the first or second time range.

8. The method of claim 4, wherein if the sensor is not stable after a predetermined maximum stabilization time, the initialization protocol is ended so that a new sensor may be connected to the sensor electronics.

9. The method of claim 8, wherein the maximum stabilization time is 30 minutes.

10. The method of claim 1, wherein the first time range is a disconnection time of greater than 120 minutes.

11. The method of claim 1, wherein the second time range is 10 minutes to 120 minutes.

12. The method of claim 1, wherein the second initialization scheme comprises application of at least two voltages to the sensor for a predetermined second initialization time.

13. The method of claim 12, wherein the at least two voltages are a series of stepped down voltages.

14. The method of claim 12, wherein the predetermined second initialization time is less than 30 minutes.

15. A method of initializing a sensor, comprising:
   determining a disconnection time, wherein the disconnection time is the amount of time a sensor has been disconnected from sensor electronics,
      wherein the sensor is an analyte sensor,
   selecting an initialization protocol based on the disconnection time, the initialization protocol selected from the group consisting of:
      a first initialization scheme comprising a first series of voltage pulses, a second initialization scheme comprising a second series of voltage pulses, and a third initialization scheme comprising the application of no voltage to the sensor,
   wherein the first initialization scheme is selected if the disconnection time falls within a first time range, the second initialization scheme is selected if the disconnection time falls within a second time range, and the third initialization scheme is selected if the disconnection time is less than the first time range and the second time range;
   applying the selected initialization protocol to the sensor; and
   applying a stabilization voltage to the sensor for a first stabilization time.

16. A method of initializing a sensor, comprising:
   determining a disconnection time, wherein the disconnection time is the amount of time a sensor has been disconnected from sensor electronics,
      wherein:
         the sensor is an analyte sensor; and
         the determining a disconnection time includes measuring the current output of the sensor and comparing the measured current output to a disconnection threshold value,
   selecting an initialization protocol based on the disconnection time, the initialization protocol selected from the group consisting of:
      a first initialization scheme comprising a first series of voltage pulses and a second initialization scheme comprising a second series of voltage pulses,
   wherein the first initialization scheme is selected if the disconnection time falls within a first time range and the second initialization scheme is selected if the disconnection time falls within a second time range; and
   applying the selected initialization protocol to the sensor.

17. The method of claim 16, wherein the determining a disconnection time further includes comparing the current output to a reconnection threshold value.

18. The method of claim 16, wherein the disconnection threshold value is 0.6 nA.

19. A method of initializing a sensor, comprising:
   determining a disconnection time, wherein the disconnection time is the amount of time a sensor has been disconnected from sensor electronics,
      wherein the sensor is an analyte sensor,
   selecting an initialization protocol based on the disconnection time, the initialization protocol selected from the group consisting of:

a first initialization scheme comprising a first series of voltage pulses and a second initialization scheme comprising a second series of voltage pulses, wherein the first initialization scheme is selected if the disconnection time falls within a first time range and the second initialization scheme is selected if the disconnection time falls within a second time range; and applying the selected initialization protocol to the sensor, and further wherein detecting hydration of the sensor prior to applying the selected initialization protocol, wherein detecting hydration includes:

applying a series of hydration pulses to the sensor for a first hydration time;

recording the current response of the sensor during application of the series of hydration pulses; and comparing the current response to a predetermined hydration threshold.

20. The method of claim 19, wherein application of the series of hydration pulses is terminated if the current response reaches or exceeds the predetermined hydration threshold.

21. The method of claim 19, wherein the detecting hydration further includes applying a second series of hydration pulses to the sensor for a second hydration time if the current response does not reach the predetermined hydration threshold during the first predetermined hydration time.

22. The method of claim 19, wherein the predetermined hydration threshold is 100 nA.

* * * * *